(12) United States Patent
Ramer

(10) Patent No.: US 10,866,638 B2
(45) Date of Patent: *Dec. 15, 2020

(54) NEURAL CONTROL OF CONTROLLABLE DEVICE

(71) Applicant: ABL IP HOLDING LLC, Conyers, GA (US)

(72) Inventor: David P. Ramer, Reston, VA (US)

(73) Assignee: ABL IP HOLDING LLC, Conyers, GA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/217,543

(22) Filed: Dec. 12, 2018

(65) Prior Publication Data
US 2019/0294245 A1    Sep. 26, 2019

Related U.S. Application Data

(63) Continuation-in-part of application No. 15/934,083, filed on Mar. 23, 2018, now Pat. No. 10,551,921, and
(Continued)

(51) Int. Cl.
*G06F 3/01*        (2006.01)
*A61B 5/04*        (2006.01)
(Continued)

(52) U.S. Cl.
CPC ............ *G06F 3/015* (2013.01); *A61B 5/0006* (2013.01); *A61B 5/04001* (2013.01);
(Continued)

(58) Field of Classification Search
None
See application file for complete search history.

(56) References Cited

U.S. PATENT DOCUMENTS 6,473,639 B1 * 10/2002 Fischell ............... A61B 5/0476
                                                                600/544
8,457,705 B2 *  6/2013 Shoureshi ............ A61B 5/0059
                                                                600/323
(Continued)

OTHER PUBLICATIONS

Notice of Allowance for U.S. Appl. No. 15/948,448, dated Feb. 13, 2020, 11 pages.
(Continued)

*Primary Examiner* — Ramesh B Patel
(74) *Attorney, Agent, or Firm* — RatnerPrestia

(57) ABSTRACT

A system includes a controllable device configured to provide a premises related service in an area. The system includes a neural device to be positioned with respect to a part of a body of a user and circuitry to process nerve signals detected in real-time. The system also includes a processor in communication with the circuitry, a memory and instructions stored in the memory for execution by the processor. Data stored in the memory associates each of some number of predetermined sets of nerve signals with a control instruction. Execution of the instructions configures the processor to use the stored data to analyze the real-time detected nerve signals to determine when real-time detected nerve signals correspond to one of the predetermined sets of nerve signals and generate a control data signal based on the associated control instruction to cause a controller to control an operation of the controllable device.

5 Claims, 14 Drawing Sheets

Related U.S. Application Data a continuation-in-part of application No. 15/948,448, filed on Apr. 9, 2018, now Pat. No. 10,682,099, which is a continuation-in-part of application No. 15/934,083, filed on Mar. 23, 2018, now Pat. No. 10,551,921, application No. 16/217,543, filed on Dec. 12, 2018, which is a continuation-in-part of application No. 15/981,446, filed on May 16, 2018, now Pat. No. 10,682,069, which is a continuation-in-part of application No. 15/948,448, filed on Apr. 9, 2018, now Pat. No. 10,682,099, which is a continuation-in-part of application No. 15/934,083, filed on Mar. 23, 2018, now Pat. No. 10,551,921.

(51) Int. Cl.

| | | |
|---|---|---|
| *G05B 19/042* | (2006.01) | |
| *A61B 5/0476* | (2006.01) | |
| *H05B 47/10* | (2020.01) | |
| *A61B 5/00* | (2006.01) | |
| *A61B 5/0496* | (2006.01) | |
| *H04L 29/08* | (2006.01) | |
| *G06F 21/32* | (2013.01) | |
| *G06N 3/02* | (2006.01) | |

(52) U.S. Cl.

CPC .......... *A61B 5/0476* (2013.01); *A61B 5/0496* (2013.01); *G05B 19/042* (2013.01); *H05B 47/10* (2020.01); *A61B 2503/12* (2013.01); *G05B 2219/25011* (2013.01); *G05B 2219/25257* (2013.01); *G06F 21/32* (2013.01); *G06F 2221/2141* (2013.01); *G06N 3/02* (2013.01); *H04L 67/12* (2013.01)

(56) References Cited

U.S. PATENT DOCUMENTS

| | | | | |
|---|---|---|---|---|
| 9,449,446 | B1* | 9/2016 | Mullin | G06F 3/015 |
| 10,029,067 | B2* | 7/2018 | Gerdes | A61B 5/0478 |
| 10,223,633 | B2* | 3/2019 | Breuer | G06N 3/02 |
| 10,551,921 | B2* | 2/2020 | Ramer | A61B 5/6814 |
| 2014/0257073 | A1* | 9/2014 | MacHon | A61B 5/04012 |
| | | | | 600/383 |
| 2014/0354534 | A1* | 12/2014 | Mullins | G06F 3/013 |
| | | | | 345/156 |
| 2015/0282760 | A1* | 10/2015 | Badower | A61B 5/6803 |
| | | | | 600/383 |
| 2016/0103487 | A1* | 4/2016 | Crawford | A61B 5/0484 |
| | | | | 600/544 |
| 2016/0143554 | A1* | 5/2016 | Lim | A61B 5/6814 |
| | | | | 600/383 |
| 2016/0198971 | A1* | 7/2016 | Adachi | G06F 19/325 |
| | | | | 600/379 |
| 2016/0360970 | A1* | 12/2016 | Tzvieli | A61B 5/6803 |
| 2017/0172497 | A1* | 6/2017 | Marquez Chin | G16H 50/20 |
| 2017/0199569 | A1* | 7/2017 | Cruz-Hernandez | G06F 3/016 |
| 2017/0228512 | A1* | 8/2017 | Driscoll | H04L 67/1097 |
| 2018/0092557 | A1* | 4/2018 | Bickford | A61B 5/0245 |
| 2018/0184974 | A1* | 7/2018 | Cimenser | A61B 5/6803 |
| 2018/0285540 | A1* | 10/2018 | Chen | G06F 21/32 |
| 2018/0317848 | A1* | 11/2018 | Gunasekar | A61B 5/7246 |
| 2018/0368722 | A1* | 12/2018 | Lunner | G06F 3/013 |
| 2019/0121431 | A1* | 4/2019 | Lee | G06F 3/015 |
| 2019/0122475 | A1* | 4/2019 | Dyne | G07C 9/30 |
| 2019/0159675 | A1* | 5/2019 | Sengupta | A61B 5/0024 |
| 2019/0290157 | A1 | 9/2019 | Ramer et al. | |
| 2019/0290211 | A1 | 9/2019 | Ramer et al. | |
| 2019/0294244 | A1 | 9/2019 | Ramer et al. | |
| 2019/0294245 | A1 | 9/2019 | Ramer | |
| 2020/0110464 | A1* | 4/2020 | Ramer | A61B 5/0006 |

OTHER PUBLICATIONS

Notice of Allowance for U.S. Appl. No. 15/981,446, dated Feb. 12, 2020, 11 pages.

Non Final Office Action for U.S. Appl. No. 15/934,083, dated Aug. 9, 2019, 9 pages.

Notice of Allowance for U.S. Appl. No. 15/934,083, dated Oct. 9, 2019, 8 pages.

Non Final Office Action for U.S. Appl. No. 15/948,448, dated Oct. 22, 2019, 15 pages.

Non Final Office Action for U.S. Appl. No. 15/981,446, dated Oct. 22, 2019, 15, pages.

Entire prosecution history of U.S. Appl. No. 15/934,083, entitled "Electroencephalography Control of Controllable Device," filed Mar. 23, 2018.

Entire prosecution history of U.S. Appl. No. 15/948,448, entitled "Training of an Electroencephalography Based Control System," filed Apr. 9, 2018.

Entire prosecution history of U.S. Appl. No. 15/981,446, entitled "User Preference and User Hierarchy in an Electroencephalography Based Control System," filed May 16, 2018.

"Nissan's 'B2V system lets you drive a car with brain waves", https://www/nbcnews.com/mach/science/nissan-paves-way-cars-read-your-mind-ncna834811, searched Jan. 9, 2018 (4 pages).

Wikipedia, "Consumer Computer Brain-Interfaces", https://en.wikipedia.org/wiki/Consumer_brain%E2%80%93computer_interfaces, searched Dec. 27, 2017 (2 pages).

Sophia Chen, "Hardwiring the BRAIN fNIRS technology creates an increasingly sophisticated connection between brain and computer," SPIE Professional, Jan. 2019, pp. 22-24.

OSA®, "Fiber Optic Sensor Measures Tiny Magnetic Fields," Sep. 19, 2019, Copyright © 2018 The Optical Society (4 pages).

\* cited by examiner

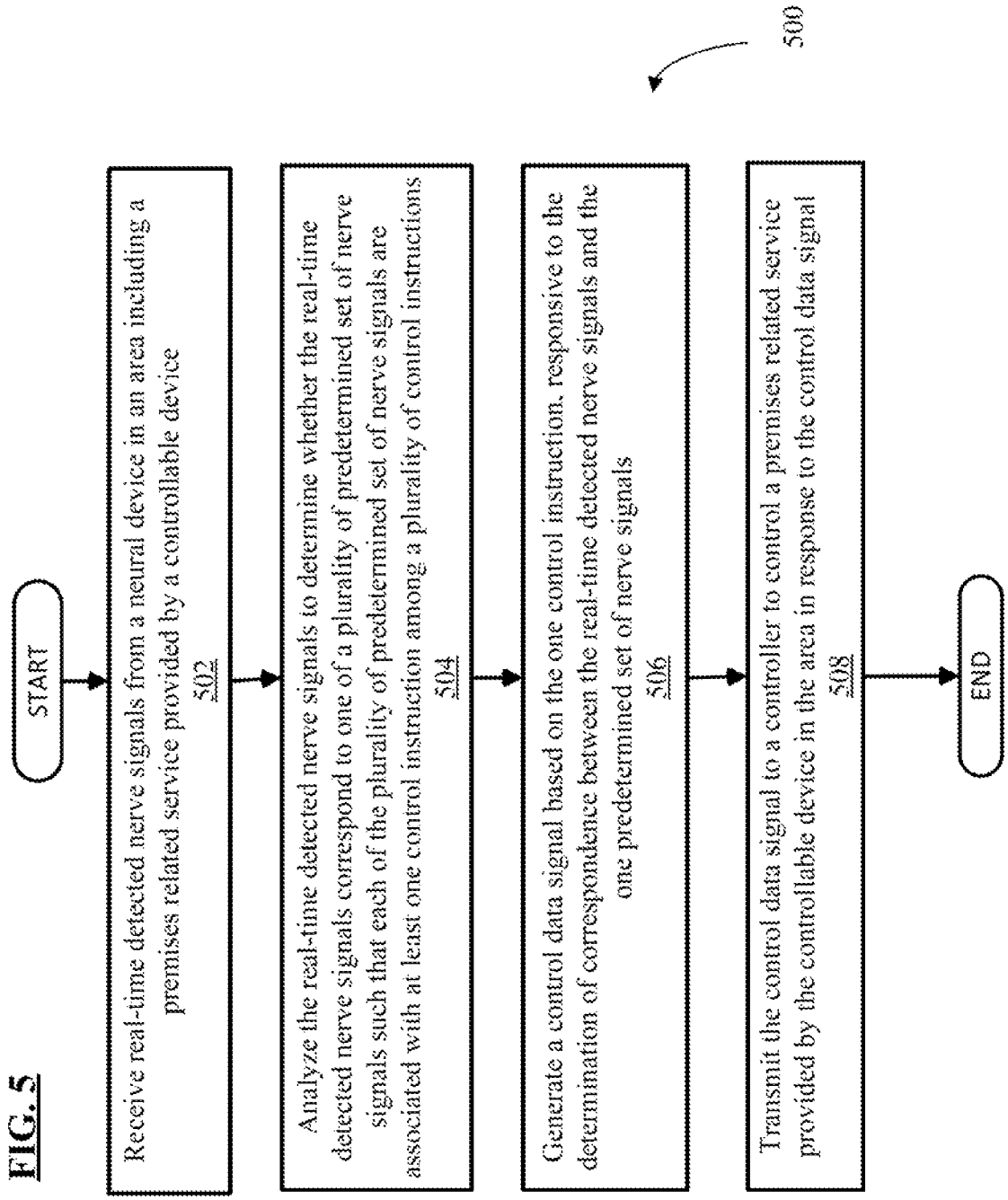

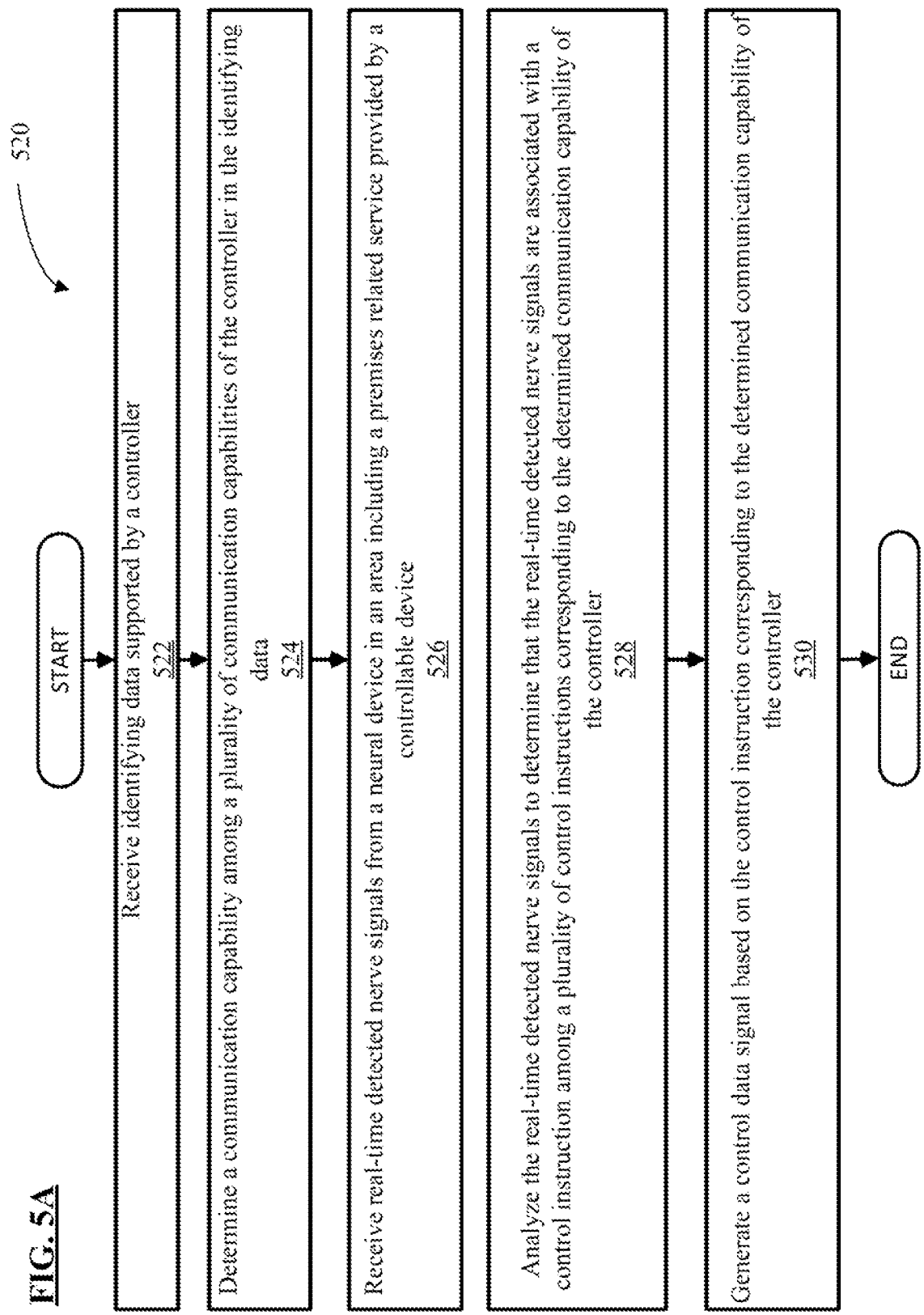

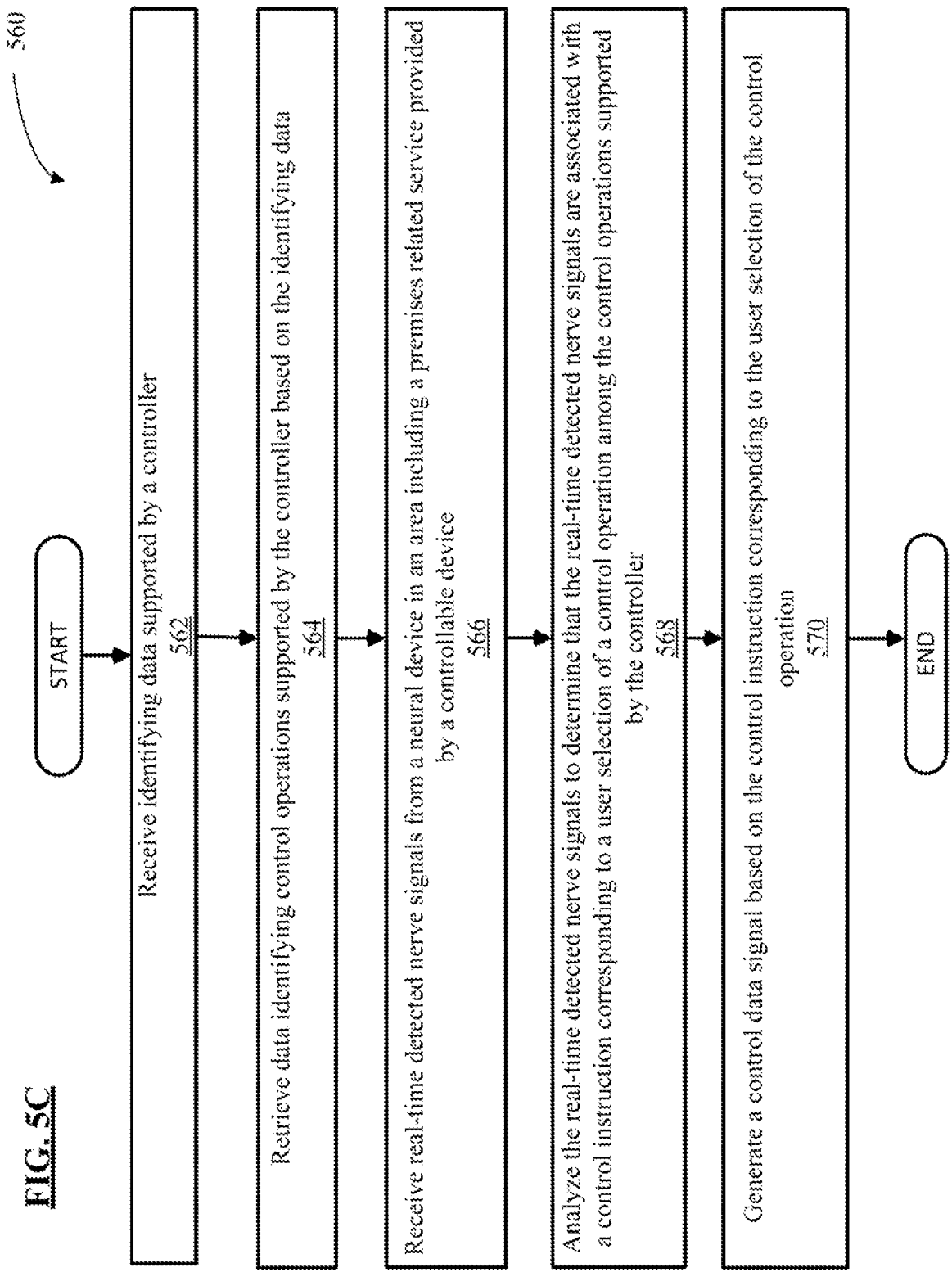

NEURAL CONTROL OF CONTROLLABLE DEVICE

RELATED APPLICATIONS

This application is a continuation-in-part of and claims priority from U.S. application Ser. No. 15/934,083, filed Mar. 23, 2018, now U.S. patent Ser. No. 10/551,921, and pending U.S. application Ser. No. 16/703,249, filed Dec. 4, 2019, which is a divisional application of U.S. patent Ser. No. 10/551,921, each of which is entitled "ELECTROEN-CEPHALOG-RAPHY CONTROL OF CONTROLLABLE DEVICE".

This application also is a continuation-in-part of and claims priority from U.S. application Ser. No. 15/948,448 filed on Apr. 9, 2018, now U.S. patent Ser. No. 10/682,099, entitled "TRAINING OF AN ELECTROENCEPHALOG-RAPHY BASED CONTROL SYSTEM;" and the U.S. patent Ser. No. 10/682,099 is a continuation-in-part of the above cited U.S. patent Ser. No. 10/551,921.

This application also is a continuation-in-part of and claims priority from U.S. application Ser. No. 15/981,446 filed May 16, 2018, now U.S. patent Ser. No. 10/682,069, entitled "USER PREFERENCE AND USER HIERARCHY IN AN ELECTROENCEPHA-LOGRAPHY BASED CONTROL SYSTEM;" the U.S. patent Ser. No. 10/682,069 is a continuation-in-part of the above cited U.S. patent Ser. No. 10/682,099; and as noted, the U.S. patent Ser. No. 10/682,099 is a continuation-in-part of the above cited U.S. patent Ser. No. 10/551,921.

The entire contents of the U.S. patent Ser. No. 10/551,921, the U.S. patent Ser. No. 10/682,099 and the U.S. patent Ser. No. 10/682,069 are incorporated herein by reference.

TECHNICAL FIELD

The subject matter of this application is directed toward control systems, more specifically to control of a controllable device such as lighting, building management or building automation control appliances, based on sensing of signals from nerves.

BACKGROUND

Electroencephalography (EEG) is an electrophysiological monitoring method to record electrical activity of the brain. It is typically noninvasive, with the electrodes placed along the scalp, although invasive electrodes are sometimes used such as in electroencephalography. EEG measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus either on event-related potentials or on the spectral content of EEG. The former investigates potential fluctuations time locked to an event like stimulus onset or button press. The latter analyzes the type of neural oscillations that can be observed in EEG signals in the frequency domain.

It has been suggested to use EEG to control devices. For example, the U.S. Air Force demonstrated in the 1980s that pilots wearing simple EEG head gear could control computer displays. Presently, EEG systems are being used to control things like "quad copters". In fact, EEG sensors may be implemented inside a head of a user. As this technology becomes more prevalent one could imagine that EEG systems could become pervasive.

Neural sensing is a monitoring method to detect and/or record neural activity of a human body. A neural device typically includes one or more nerve sensors that detect signals from the nerves in a part of a human body, for example, o activate muscles or as an indicated of a sensed condition such as touch, heat or pain. A neural device is typically placed on some part of the human body, for example, as a glove to be worn on a person's hand or as a cuff to be worn on person's wrist or forearm. Nerve sensing may be utilized on the head, for example, to detect nerve signals controlling movement of facial or scalp muscles, although the detected nerve signals are actually somewhat different from the voltage fluctuations resulting from ionic current within the neurons of the brain detected by EEG equipment. Alternatively, nerve sensors can be implanted inside the user's body. In clinical contexts, the neural monitoring refers to recording of neural activity over a period of time as recorded from multiple sensors placed on the human body.

It has been suggested to use neural sensing to control devices. For example, neural sensing systems are being used to allow a pilot to control his/her aircraft and analyze flight paths, velocity, etc. The neural sensing systems are also being used in other applications such as medical, film and video games. Nerve sensors may be implemented inside a user's body. As this technology becomes more prevalent, one could imagine that neural sensing systems could become pervasive.

In recent years, the sophistication of lighting control systems has increased significantly, for example, offering lighting scene, profile or schedule manipulation for individual lighting devices, groups of lighting devices or all lighting devices at a controlled premises. Depending on the technology of the luminaires control functions may include simple ON/OFF control, intensity control (e.g. dimming) and even control of color characteristics (e.g. for tunable white luminaires or the like). Building automation control (BAC) systems or building management systems (BMS) also have improved in the sophistication of the ability to reach every unit item or controllable appliance at the premises, offer informative, intuitive access to information and readily customizable control operations for every appliance on the premises that is adapted for BAC or BMS type networked monitoring and control functions.

Currently, no systems exist that utilize neural sensing to control lighting operations of the lighting systems and/or building management operations of the building management system.

SUMMARY

The Examples disclosed herein improve over lighting control systems and BAC systems by providing a control methodology to control the lighting and/or the building management systems based on sensing of nerve signals, e.g. by an appropriate neural device.

An example system includes a controllable device configured to provide a premises related service in an area of a premises. The system also includes a neural device configured to be positioned on a part of a body of a user. The neural device includes one or more sensors configured to detect one or more nerve signals from nerves in the part of the body of the user. The system also includes circuitry coupled to the one or more nerve sensors configured to process nerve signals detected in real-time via one or more sensors of the neural device. The system further includes a processor coupled to or in communication with the circuitry, a memory accessible by the processor, and instructions stored in the memory for execution by the processor. The memory also stores data associating each of a plurality of predetermined sets of nerve signals with a control instruction among a plurality of control instructions. The execution of the instructions configures the processor to use the stored data so as to analyze the real-time detected nerve signals to determine whether the real-time detected nerve signals correspond to one of the plurality of predetermined sets of nerve signals associated with the one of the control instruction and generate a control data signal based on the one control instruction, responsive to the determination of correspondence between the real-time detected nerve signals and a particular predetermined set of nerve signals. The system also includes a controller coupled to or in communication with the controllable device and the processor. The controller is configured to control the premises related service provided by the controllable device in the area, in response to the control data signal.

An example neural device for use on a part of a body of a user at least while in an area of a premises where a premises related service is provided by a controllable device. The neural device includes one or more nerve sensors configured to detect nerve signals from nerves in the part of the body of the user, when the neural device is positioned on the part of the body of the user. The neural device in this example also includes circuitry coupled to the one or more nerve sensors configured to process nerve signals detected in real-time via the one or more nerve sensors. The neural device further includes a processor coupled to or in communication with the circuitry, a memory accessible by the processor and instructions stored in the memory for execution by the processor. The memory also stores data associating each of a plurality of predetermined sets of nerve signals with a control instruction, among a plurality of control instructions. The execution of the program instructions by the processor configures the neural device to use the stored data to analyze the real-time detected nerve signals to determine whether the real-time detected nerve signals correspond to one of the plurality of predetermined sets of nerve signals associated with one of the control instructions. The execution of the instructions by the processor also configures the neural device to generate a control data signal based on the one control instruction, responsive to the determination of correspondence between real-time detected nerve signals and the particular predetermined set of nerve signals. The execution of the instructions by the processor further configures the neural device to transmit the control data signal to a controller coupled to or in communication with the controllable device, to control the premises related service provided by the controllable device in the area.

An example method includes receiving real-time detected signals from a neural device worn by a user in an area of a premises. The method also includes analyzing the real-time detected nerve signals to determine that the real-time detected nerve signals correspond to one of a plurality of predetermined set of nerve signals. Each predetermined set of nerve signals is associated with a control instruction from among a plurality of control instructions. The method further includes generating a control data signal based on the associated control instruction, responsive to the determination of correspondence between the real-time detected nerve signals and the one predetermined set of nerve signals. The control data signal is transmitted to a controller, to control a premises related service provided by a controllable device in the area.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 5 is an example flowchart illustrating a method for system level neural sensing control of the premises related service provided by a controllable device in an area of a premises.

FIG. 5A is another example flowchart illustrating a method for system level neural sensing control of the premises related service provided by a controllable device in an area of a premises.

FIG. 5C is a further example flowchart illustrating a method for system level neural sensing control of the premises related service provided by a controllable device in an area of a premises.

DETAILED DESCRIPTION

Figure 1:
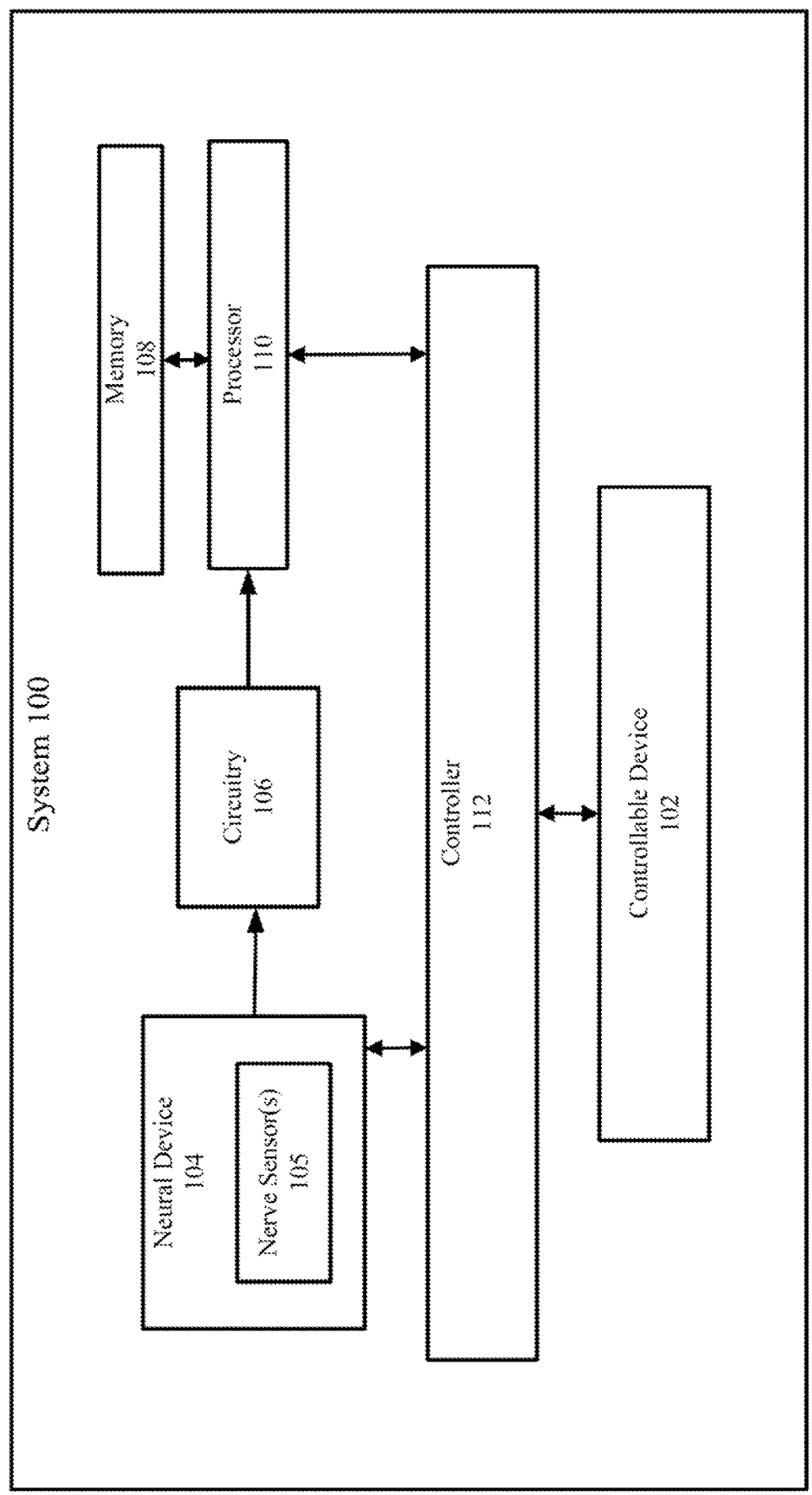
FIG. 1 illustrates one example of a neural sensing system to control a premises related service provided by a controllable device in an area of a premises.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The term "luminaire" as used herein is intended to encompass essentially any type of device that processes, generates or supplies light, for example, for general illumination of a space intended for use of or occupancy or observation, by a person or animal. However, a luminaire may provide light for use by automated equipment, such as sensors/monitors, robots, etc. that may occupy or observe the illuminated space, instead of or in addition to light provided for an organism. However, it is also possible that one or more luminaires in or on a particular premises have other lighting purposes, such as signage for an entrance or to indicate an exit. In most examples, the luminaire(s) illuminate a space or area of a premises to a level useful for a human in or passing through the space, e.g. general illumination of a room or corridor in a building or of an outdoor space such as a street, sidewalk, parking lot or performance venue. Although some types of luminaire such as skylights may passively supply light; in most of the examples described below, the actual source of illumination light in or supplying the light for a luminaire may be any type of artificial light emitting device that consumes electrical power to generate the illumination light, several examples of which are included in the discussions below.

The term "coupled" as used herein broadly encompasses physical or mechanical type structural connection between elements as well any logical, physical or electrical connection, link or the like by which signals, data, instructions or the like produced by one system element are imparted to another "coupled" element. Unless described otherwise, coupled elements or devices are not necessarily directly connected to one another and may be separated by intermediate components, elements or communication media that may modify, manipulate or carry the signals. For example, system elements may be coupled for wired or wireless communication, including without limitation radio frequency (RF), light fidelity (LiFI), fiber optic, ultrasonic or the like in the discussions below.

Various examples disclosed herein relate to a neural control methodology for lighting and building management. Examples described below encompass systems utilizing nerve signal sensing and related processing functionalities to control various BAC appliances, lighting devices, or the like that provide a service in an area of a premises. Such a service may include but is not limited to lighting, heating, ventilation and air conditioning (HVAC), door access, fire and safety equipment, on-premises surveillance, etc.

Reference is now made in detail to the examples illustrated in the accompanying drawings and discussed below.

The example of FIG. 1 illustrates a system 100 including a controllable device 102 configured to provide a premises related service in an area 101 of a premises. Such controllable device 102 may include one or more luminaires, various BAC appliances, etc. Some of the premises related services include but are not limited to lighting, heating, ventilation and air conditioning (HVAC), door access, fire and safety services, on-premises surveillance, etc.

The system 100 also includes a neural device 104, which is configured to be positioned on a part of a body of a user in the area 101. In one example, the neural device 104 is configured to be positioned on some part of the human body, for example, as a glove to be worn on a person's hand or as a cuff to be worn on a person's wrist or forearm. In another example, the neural device 104 is a neural sensor implanted inside the user's body. In another example, the neural device may be worn on the head of a user, e.g. as a mask, hat or cap.

The neural device 104 includes one or more nerve sensors 105 configured to detect nerve signals from a nervous system of the part of the body such as a finger, back, hand, forearm, face, etc. on which the neural device 104 is positioned. The system 100 also includes circuitry 106 coupled to the nerve sensors 105 to process sensor outputs based on detection of the nerve signals by the nerve sensors 105. In one example, the signals are sets of nerve signals such as nerve signals detected by the nerve sensors 105 in real time. In one example, the nerve signals are pre-determined sets of neural (nerve) signals detected by the nerve sensors 105 prior to real time, for example, for training purposes.

In one implementation, the system 100 includes a memory 108 that stores data, which associates each of the plurality of pre-determined sets of nerve signals from the nerves of the part of the body prior to the real time with at least one control instruction among a plurality of control instructions that may be generated to control one or more premises related services. Each control instruction corresponds to a particular aspect (e.g. state change or parameter setting) for controlling the premises related service provided by the controllable device 102. In one example, the controllable device is either a luminaire or a BAC appliance. As such, the control instruction is configured for controlling either the luminaire or the BAC appliance. The system 100 also includes a processor 110, which is coupled to the circuitry 106 to receive the processed sets of real-time detected nerve signals. The memory 108 also stores instructions, which is accessible by the processor 110 such that execution of the instructions by the processor 110 to perform various functions described herein.

In one implementation, the processor 110 analyzes the real-time detected nerve signals to determine whether the real-time detected nerve signals correspond to one of the plurality of pre-determined sets of nerve signals stored in the memory 108. Upon determining that the real-time detected nerve signals corresponds to one of the pre-determined sets of nerve signals, the processor 110 determines at least one control instruction associated with the corresponding pre-determined set of nerve signals. The processor 110 selects one of the luminaire or the BAC appliance based on the at least one control instruction. The processor 110 generates a control data signal for the selected luminaire or the BAC appliance based on the at least one control instruction. In one example, the processor 110 converts the control instruction into a control data signal, which indicates to the luminaire or the BAC appliance an action related to controlling premises related service in the area 101.

As illustrated, the system 100 also includes a controller 112 coupled to or in communication with the controllable device 102 and the processor 110. In one example, the controller 112 is an intelligent element integrated in the controllable device 102. In another example, the controller is a centralized controller controlling a plurality of similar controllable devices, (e.g. wall switch or like controlling a number of the luminaires or a building management control system configured to communicate with and control the controllable device and other types of controllable devices within the premises).

In one implementation, the processor 110 transmits the control data signal to a controller 112, which controls the premises related service provided by the controllable device 102 (selected luminaire or the BAC appliance) in the area 101. Some examples of controlling the premises related services include, but are not limited to turning lights ON or OFF, dimming lights, adjust color temperature of the light, adjusting light color between red green blue, adjustments for circadian rhythm, chaotic program adjustment of lighting or HVAC operations, individual luminaire control, occupancy sensing, decrease or increase level of one of heating, cooling or air, open or close doors, open or close the doors, turn on or off the television, decrease or increase the sound of alarm system, etc.

In some implementations, the processor 110 determines that real-time detected nerve signals do not correspond to one of the plurality of pre-determined sets of nerve signals stored in the memory 108. As such, the processor 110 does not recognize such real-time detected nerve signals as corresponding to a known instruction for operation of lighting or other building management systems. In one example, the processor 110 ignores such real-time detected nerve signals. In another example, the processor 110 may search for other types of pre-determined sets of nerve signals that support other types of inputs. For example, the PIOT device may support control instructions to other types of equipment (e.g. a Television set). In one example, in a training mode, the system updates relevant data such as the pre-determined set of nerve signals corresponding to a particular control instruction when the real-time nerve signals are not recognized as a known instruction. For example, the system updates or adds pre-determined set of nerve signals based on an input from a trusted detector indicating the type of control instruction the user intended to selection via the unrecognized real-time detected nerve signals. Further, in the training mode, the configuration and/or settings are provided to help the neural device and/or the PIOT device to learn to associate the nerve signals with user's desired control instruction. Additional information regarding training may be found in the above-incorporated Ser. No. 15/948,448 application.

Figure 2:
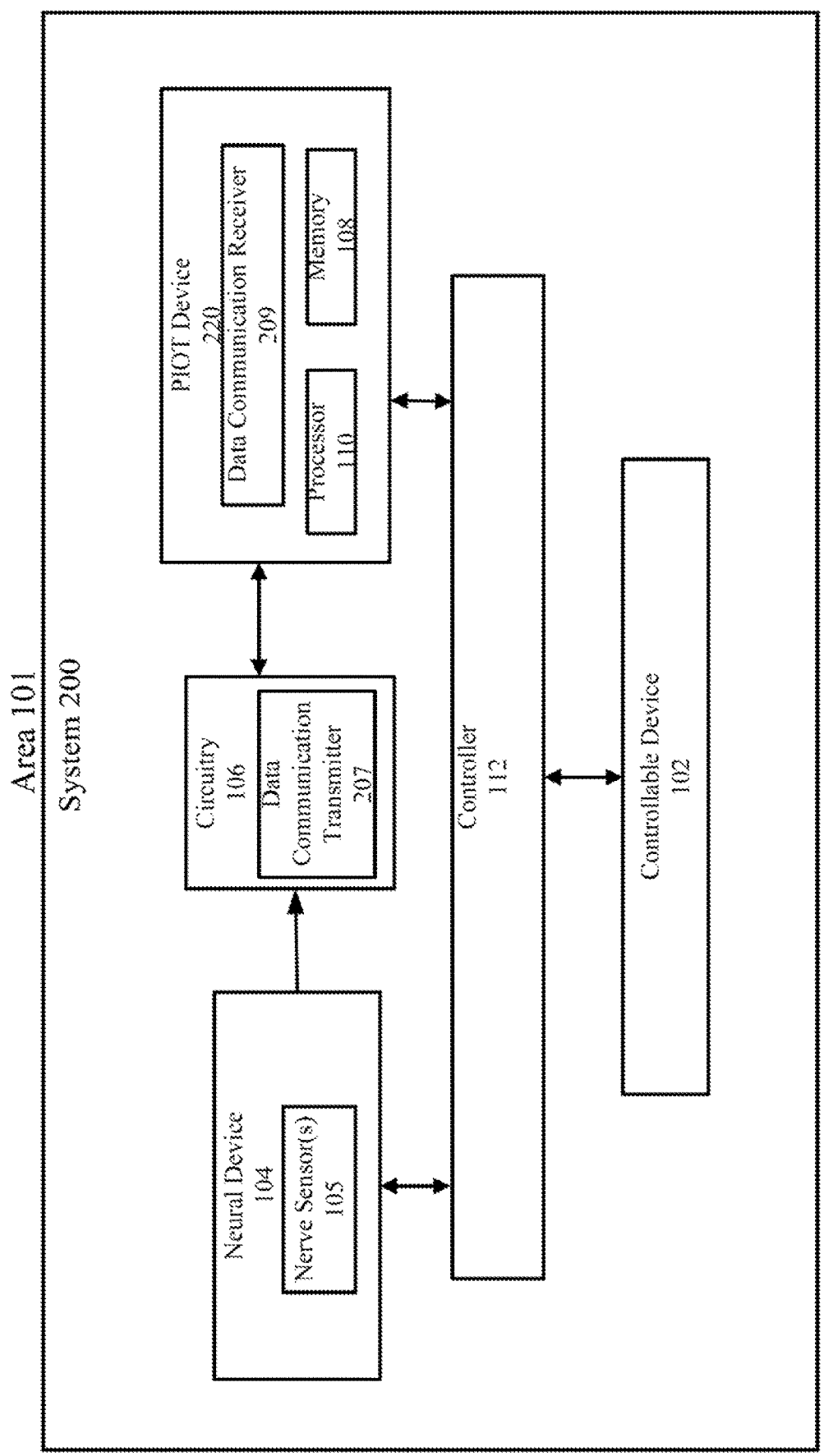
FIG. 2 illustrates another example of a neural sensing system to control a premises related service provided by a controllable device in an area of a premises.

FIG. 2 includes an example of the system 200, which includes some of the same components of system 100, and the circuitry 106 further includes a data communication transmitter 207. The system 200 also includes a personal Internet of Things (PIOT device) 220 that, in this example, includes the memory 108 and the processor 110 and further includes a data communication receiver 209. The data communication receiver 209 is compatible with the data communication transmitter 207 of the circuitry 106. In one example, the data communication transmitter 207 and data communication receiver 209 are a radio frequency (RF) devices configured to transmit or received data respectively, over a band of RF spectrum.

The RF spectrum or "radio spectrum" is a non-visible part of the electromagnetic spectrum, for example, from around 3 MHz up to approximately 3 THz, which may be used for a variety of communication applications, radar applications, or the like. In the discussions above, the RF transmitted and received for communication, e.g. Wifi, Bluetooth Low Energy (BLE), Zigbee etc., also may be used for neural responsive control of lighting or a building management control system, via the frequencies bands/bandwidths specified for those standard wireless RF spectrum data communication technologies. In another implementation, the network communications media may be wired, fiber optic, LiFI, ultrasonic or the like.

In another implementation, the transmitter and receiver are ultra-wide band (also known as UWB, ultra-wide band and ultra-band) devices. UWB is a radio technology that can use a very low energy level for short-range, high-bandwidth communications over a large portion of the radio spectrum. UWB does not interfere with conventional narrowband and carrier wave transmission in the same frequency band. Ultra-wideband is a technology for transmitting information spread over a large bandwidth (>500 MHz) and under certain circumstances be able to share spectrum with other users. Ultra-wideband characteristics are well-suited to short-distance applications, such as short-range indoor applications. High-data-rate UWB may enable wireless monitors, the efficient transfer of data from digital camcorders, wireless printing of digital pictures from a camera without the need for a personal computer and file transfers between cell-phone handsets and handheld devices such as portable media players. UWB may be used in a radar configuration (emitter and deflection detection at one node) for real-time location systems and occupancy sensing/counting systems; its precision capabilities and low power make it well-suited for radio-frequency-sensitive environments. Another feature of UWB is its short broadcast time. Ultra-wideband is also used in "see-through-the-wall" precision radar-imaging technology, precision detecting and counting occupants (between two radios), precision locating and tracking (using distance measurements between radios), and precision time-of-arrival-based localization approaches. It is efficient, with a spatial capacity of approximately 1013 bit/s/m$^2$.

In one implementation, the memory 108 stores user identification data (e.g. user specific or group identifiers) for each of a plurality of users. In one example, the user identification data is uniquely associated with the neural device 104 identifying a particular user of the neural device 104 among a plurality of users who may be in the area 101 of the premises from time to time. In another example, the user identification data may uniquely associated with the neural sensor device 104 identifying a user among a group of users of the particular neural device 104 when that device 104 is in the area 101 of the premises. In a further example, the user identification data may uniquely associated with the PIOT device 220 identifying a user of the PIOT device 220 among the plurality of users of the PIOT device 220 or among a more general group of users who may be in the area 101 of the premises (but using other similar device). The user's location may be tracked based on the user identification data associated with one or both of the neural device 104 or the PIOT device 220.

A similar approach, for a user having a number of neural sensing devices on different parts of the body may recognize an instruction and recognizing additional related user inputs for refining the resulting command data. In such an implementation, the user may have a neural sensing device on the head or on one hand or wrist and another similar device on the other hand or wrist. In such an example, the same or a second memory 108 stores second data, which associates each of a plurality of pre-determined second sets of nerve signals from nerves of a second part of the body detected via one or more sensors 105 of the second neural device (otherwise similar to device 104) with at least one pre-determined user input among a plurality of pre-determined user inputs. In one use case example, a person may have the first neural device 104 positioned on the person's wrist for instruction inputs (e.g. dim the lights) and another neural device 104 positioned on the person's hand to detect nerve signals to the fingers as an additional user input (e.g. increase or decrease when dimming and/or how much to change light intensity). In one example, for the additional input, circuitry like 106 processes the nerve signals received from the one or more nerve sensors 105 of the other neural device 104. The circuitry also includes the data communication transmitter 107, which functions to transmit the processed nerve signals to the PIOT device 220. In one example, the processor 110 configures the other neural device 104 to receive data regarding the real-time detected nerve signals and uses the stored second data to analyze the received data to determine whether the real-time detected nerve signals correspond to one of the plurality of pre-determined sets of nerve signals associated with one of the determined additional user inputs. The control data signal based on detection of never signals via the first neural device is performed as in earlier examples. In addition, the processor 110 determines that the real-time nerve signals detected via the second neural device correspond to the one pre-determined set of nerve signals associated with one of the determined additional user inputs. In response, the processor 110 generates the control data signal (e.g. as was selected based on the instruction identified from processing signals from the first neural device) further based on the pre-determined additional user input. In the dimming example, the control data signal may indicate dimming, whether up or down, and a percentage or the like for light intensity. The processor 110 transmits the resultant control data signal to the controller 112 coupled or in communication with the controllable device 102.

In one implementation, the memory 108 also stores a plurality of hierarchical classes of user(s) as member(s) with each class having permissions to use one or more control instructions among the plurality of control instructions. Some examples of classes of users include, building administrator, employee, guest etc. For example, the building administrator has permissions to all the control instructions while the guest may only have permissions to one or two control instructions. In one implementation, the data communication receiver 209 receives a user identification data from the neural device 104. In one implementation, the data communication receiver 209 receives a user identification data directly from the PIOT device 220. The processor 110 utilizes the received user identification data to search the memory 108 to identify the user among the plurality of users and the corresponding hierarchy class of the identified user of which the user is the member. The processor 110 transmits the control data signal to the controller 112 that relates to the one or more control instructions permitted for the corresponding hierarchy class. The controller 112 controls the premises related service provided by the controllable device 102 (selected luminaire or the BAC appliance) in the area 101 based on the permitted one or more control instructions. Additional information regarding hierarchical control may be found in the above-incorporated Ser. No. 15/981,446 application.

In one implementation, the data communication receiver 209 also receives identifying data from the controller 112. The identifying data includes but is not limited to location of the controller in the area, communication capabilities of the controller, control operations supported by the controller, types of controllable devices controlled by the controller, controller variables for each type of controllable device, or combinations thereof.

In one example, the communication capabilities are supported by the neural device 104. In another example, the communication capabilities are supported by the PIOT device 220. The control operations supported by the controller 112 may include light related control operations, building related control operations etc. Some examples of supported light related control operations include turning lights on/off, dimming lights, color temperature, color red green blue, circadian rhythm, chaotic program etc. Building related examples of supported control operations include heating/cooling & air control, door access controls, fire and safety control, on-premises surveillance control etc. As discussed above, types of example controllable devices include different types of luminaires, various BAC appliances etc. The controllable variables for each type of the controllable device are variables specific to the controllable device. In one example, the controllable variables may include but is not limited to various types of color characteristics, intensity of light, tuning light, rate of air flow, humidity level, temperature range, open/close of the doors/windows etc.

The memory 108 also stores instructions, which are accessible by the processor 110 such that execution of the instructions by the processor 110 to perform various functions described herein.

In one implementation, the processor 110 determines a communication capability among the plurality of communication capabilities of the controller 112 based on the controller identification data. The processor 110 functions to adapt at least one aspect of the control data signal that is to be sent to the controller 112 in response to a detected set of nerve signals based on the determined communication capability of the controller 112. In one example, the processor 110 adapts a format of the command signal of the control data signal to match with the command signal protocol of the determined communication capability of the controller 112. In another implementation, the processor 110 determines a type of the controllable device 102 among the plurality of types of controllable devices based on the identifying data. In one implementation, the processor 110 adapts the control data signal that is to be sent to the controller 112 in response to a detected set of nerve signals to the determined type of the controllable device 102. In one example, the controllable device 102 is white LED luminaire that supports ON/OFF and dimming functions, thus the processor 110 adapts the control data signal associated with the control instruction to turn the white LED luminaire ON/OFF or dim the white LED luminaire. In another example, the controllable device 102 is a specific LED luminaire that supports a specific intensity variation (such as 10%, 20% etc.) among the several intensity variations of the dimming functions. In this later example, the processor 110 adapts the control data signal associated with the control instruction to the specific intensity variation of the dimming function of the particular LED luminaire. In a further example, the controllable device 102 is a HVAC component that supports functions such as increase/decrease in temperature in the area; and in such an example, the processor 110 adapts the control data signal associated with the control instruction to increase or decrease the temperature in the area.

In one implementation, the processor 110 retrieves data identifying control operations supported by the controller based on the identifying data from the controller 112. As discussed above, the control operations supported by the controller may include light related control operations, building related control operations etc. Some of the light related control operations may include turning lights on/off, dimming lights, color temperature, color red green blue, circadian rhythm, chaotic program etc. Building related control operations may include heating/cooling & air control, door access controls, fire and safety control, on-premises surveillance control etc.

In one implementation, the processor 110 sends the data identifying control operations to an output device (not shown) of the user via the data communication transmitter 209. In one example, the control instruction corresponds to a user selection of a control operation among the identified control operations supported by the controller 112.

In one implementation, the memory 108 stores user preference data associated with the user identification data. In one example, the user preference data includes a preferred user selection of one or more control operations among the identified control operations in the identifying data that are supported by controller 112 in the area 101. In one implementation, upon receipt of the identifying data, the processor 110 accesses the memory 108 to retrieve the user preference data for the user associated with the controller 112. The processor 110 sends the user preference data to an output of the user device (not shown). In one example the control instruction corresponds to the user preference data including the preferred user selection of the one or more control operations among the identified control operations supported by the controller 112. Additional information regarding user preferences in the control functions may be found in the above-incorporated Ser. No. 15/981,446 application.

Figure 3:
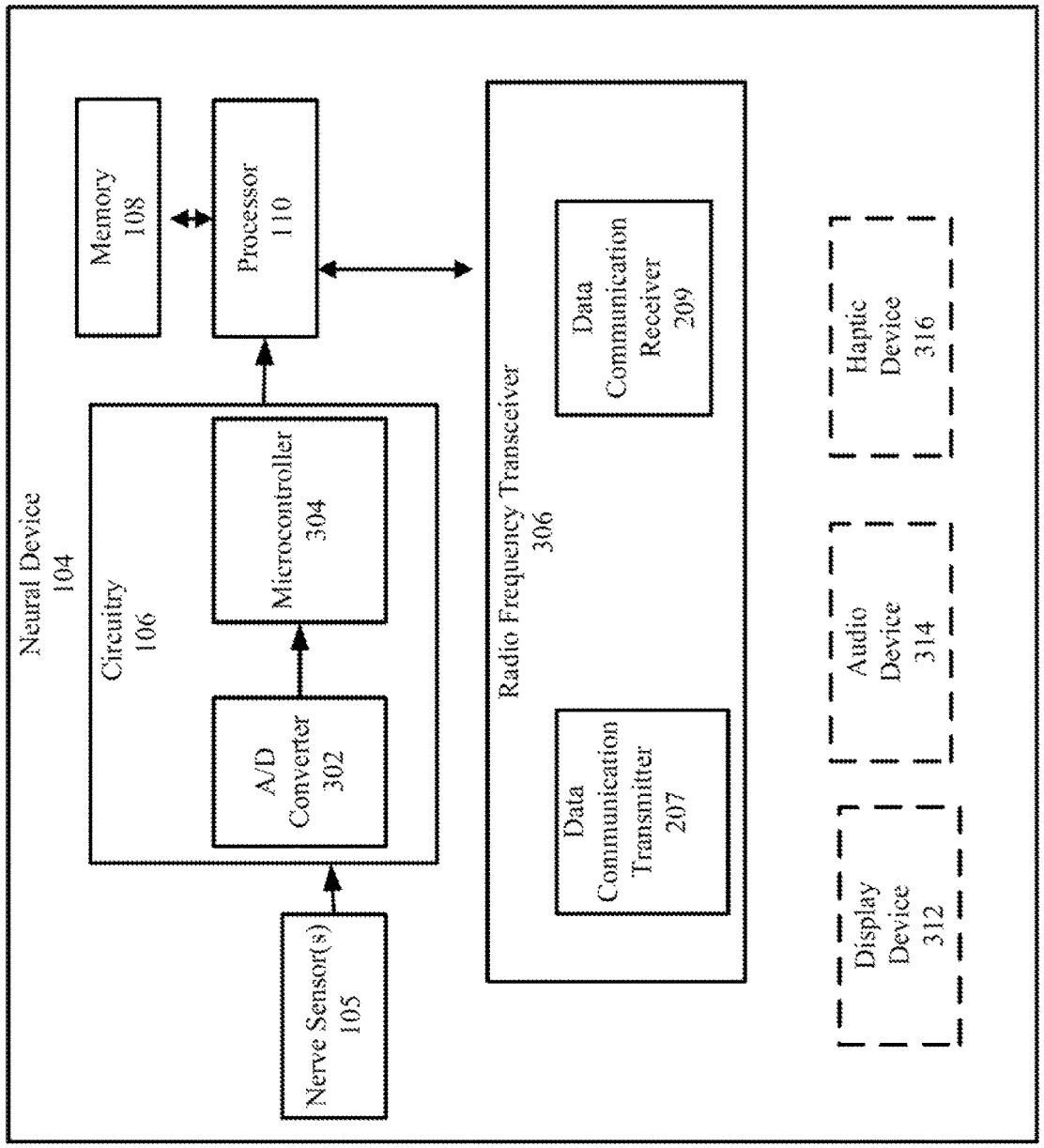
FIG. 3 is a functional block diagram example of a neural device to control a premises related service provided by a controllable device in an area of a premises.

FIG. 3 includes an example of a neural device 104 of FIG. 1. In this example, besides the nerve sensors 105, the neural device 104 also includes the circuitry 106, the memory 108 and the processor 110. As shown, the circuitry 106 includes an analog to digital (A/D) converter 302 and a microcontroller 304. As discussed above, the circuitry 106 processes the nerve signals detected in real-time by the nerve sensors 105. The nerve signals detected by the nerve sensors 105 are analog signals. In one example, A/D converter 302 converts the analog signals into digital signals, and the microcontroller 304 assembles the digital signals outputted from the A/D converter 302 into a format for a transmission to the processor 110.

The neural device 104 includes a radio frequency (RF) transceiver 306 coupled to the processor 110. Although shown separately, functions of the microcontroller 304 and processor 110 and/or memory 108 may combined, e.g. into a single system on a chip microcontroller. The RF transceiver 306 includes the data communication transmitter 207 and the data communication receiver 209. The data communication transmitter 207 transmits data or instructions over the RF spectrum. If the processor 110 in the neural device is programmed and has the data to analyze the digital signals representing the real-time detected nerve signals to determine correspondence to one of the predetermined sets of nerve signals; and then the data communication transmitter 207 transmits the control data signal based on the associated control instruction to cause the controller to control an operation of the controllable device.

FIG. 3 shows a display device 312, an audio device 314, and a haptic device 316 (in dotted line boxes), for providing perceptible information or 'feedback' to a user of the neural device 104. One or more of the display devices 312 to 315 may be included in the neural device 104 and operated via the processor 110 and appropriate driver circuitry (not separately shown); but in many examples the devices 312 to 315 may be part of or coupled to some other equipment such as a PIOT or portable user terminal device separate from but in communication with the neural device 104 via wireless RF communications and the transceiver 306.

The data communication receiver 209 may receive data over the RF spectrum, for various purposes. For example, the data communication transmitter 207 may re-transmit some received data over the RF spectrum to a user device (e.g. hosting or coupled to the display device 312, the audio device 314, and/or the haptic device 316) of the user. In other examples, the data communication receiver 209 receives data over the RF spectrum identifying the controller and/or the controllable device or possibly indicating capabilities of the controller and/or the controllable device.

The processor 110 is coupled to the circuitry 106, the transmitter 207 and receiver 209 of the transceiver 306, and the memory 108. Processor execution of programming from the memory 108 configures the neural device 104 to receive the data regarding the real-time detected nerve signals and perform other functions related to nerve signal responsive control as discussed herein. For example, where the neural device performs the analysis, etc. internally, the processor 110 and its program execution configure the neural device 104 to use stored data to analyze the received digitized nerve signal data to generate the control data signal and transmit the control data signal to the controller 112 coupled or in communication with the controllable device 102 as discussed in detail above with respect to FIG. 1.

As discussed above, in one implementation, the memory 108 stores the user identification data uniquely associated with the neural device 104 identifying a user among a plurality of users of the neural device 104 in the area 101 of the premises. Also discussed above, in one implementation, the memory 108 also stores a plurality of hierarchical classes of user(s) as member(s) with each class having permissions to use one or more control instructions among the plurality of control instructions. In one implementation, the data communication receiver 209 receives a user identification data intending to use/operate the neural device 104. As discussed above, the processor 110 utilizes the received user identification data to search the memory 108 to identify the user among the plurality of users and the corresponding hierarchy class of the identified user for a user-group/class of which the user is the member. The processor 110 transmits the control data signal to the controller 112 that relates to the one or more control instructions permitted for the corresponding hierarchy class.

As discussed above, in one implementation, the data communication receiver 209 receives identifying data from the controller 112. Also, the controller identifying data includes or allows lookup of controller related information, such as but not limited to location of the controller in the area and/or premises, communication capabilities of the controller, control operations supported by the controller, types of controllable devices controlled by the controller, controller variables for each type of controllable device, or combinations thereof.

As discussed above, in one implementation, the processor 110 determines a communication capability among the plurality of communication capabilities of the controller based on the identifying data. The processor 110 functions to adapt at least one aspect of the control data signal based on the determined communication capability of the controller 112. Also, as discussed above, in another implementation, the processor 110 determines a type of the controllable device 102 among the plurality of types of controllable devices based on the identifying data. In one implementation, the processor 110 adapts the control data signal to the determined type of the controllable device 102.

As discussed above, in one implementation, the processor 110 retrieves data identifying control operations supported by the controller based on the identifying data from the controller 112. The processor 110 sends the data identifying control operations to an output device (e.g., having the display device 312, audio device 314 and/or haptic device 316) of the user via the data communication transmitter 209. In one example, the control instruction corresponds to a user selection of a control operation among the identified control operations supported by the controller 112.

As discussed above, in one implementation, the memory 108 stores user preference data associated with the user identification data. In one example, the user preference data includes a preferred user selection of one or more control operations among the identified control operations in the identifying data that are supported by controller 112 in the area 101. Also, as discussed above, in one implementation, upon receipt of the identifying data, the processor 110 accesses the memory 108 to retrieve the user preference data for the user associated with the controller 112. The processor 110 sends the user preference data to an output device (e.g. having the display device 312, audio device 314 and/or the haptic device 316) of the user device via the data communication transmitter 209. In one example, the control instruction corresponds to the user preference data including the preferred user selection of the one or more control operations among the identified control operations supported by the controller 112.

Figure 4:
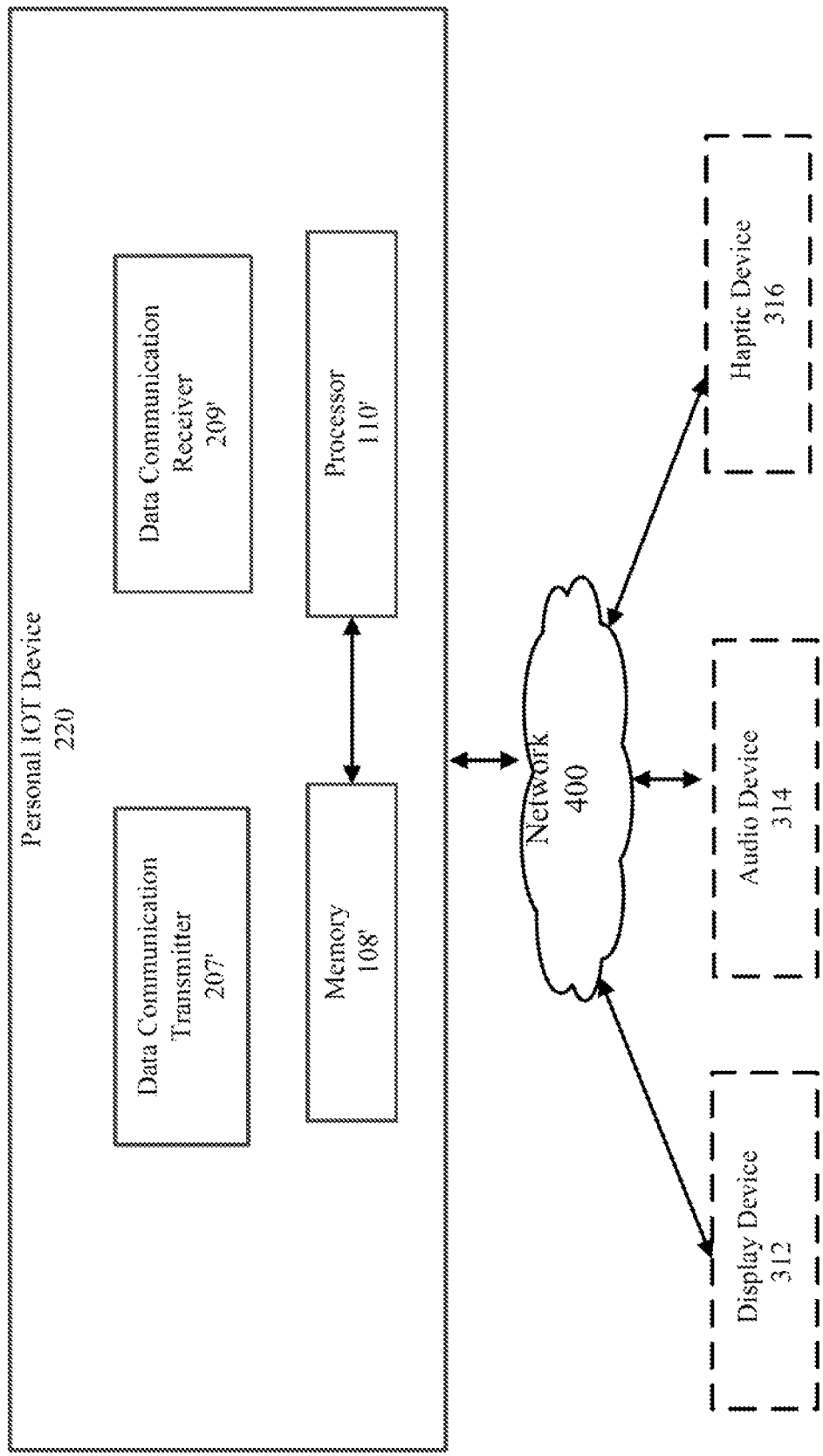
FIG. 4 is a functional block diagram of an example of a personal Internet of Things (PIOT) device to control a premises related service provided by a controllable device in an area of premises, based on neural sensing.

FIG. 4 illustrates an example of a PIOT device 220 that may be used in a system like that of FIG. 2. In this illustrated example, the PIOT device 220 includes the memory 108' and the processor 110' for the analysis and command signal data generation functions, as well as a data communication transmitter 207' and a data communication receiver 209'. The data communication transmitter 207' and the data communication receiver 209' are similar to and/or compatible with data communication receiver 209 and the data communication transmitter 207 of the neural device 104 of FIG. 3. The data communication receiver 209' for example may receive the digitized data representing the detected nerve signals for analysis by the processor 110' using data stored in the memory 108'. In such an arrangement, the processor 110' in the PIOT device is programmed and uses the data to analyze the digital signals representing the real-time detected nerve signals to determine correspondence to one of the predetermined sets of nerve signals, then the data communication transmitter 207' transmits the control data signal based on the associated control instruction to cause the controller to control an operation of the controllable device.

FIG. 4 shows the display device 312, the audio device 314, and the haptic device 316 (in dotted line boxes), for providing perceptible information or 'feedback' to a user of the neural device and the PIOT device 220. In this example the devices 312 to 315 may be part of or coupled to some other equipment such as a portable user terminal device separate from but in communication with the PIOT device 104 via the network 400 and wireless RF communications at least from network 400 with the transmitter 207' and receiver 209' of the PIOT device 220.

The data communication receiver 209' may receive data over the RF spectrum, for various purposes. For example, the data communication transmitter 207' may re-transmit some received data over the RF spectrum to the network 400 for communication to the user device hosting or coupled to one or more of the display device 312, the audio device 314, and/or the haptic device 316) of the user. In other examples, the data communication receiver 209' receives data over the RF spectrum identifying the controller and/or the controllable device or possibly indicating capabilities of the controller and/or the controllable device.

The processor 110' is coupled to the transmitter 207', the receiver 209' and the memory 108'. Processor execution of programming from the memory 108' configures the PIOT device 220 to receive the data regarding the real-time detected nerve signals and perform other functions related to nerve signal responsive control as discussed herein. For example, the processor 110' and its program execution configure the PIOT device 220 to use stored data to analyze the received digitized nerve signal data to generate the control data signal and transmit the control data signal to the controller 112 coupled or in communication with the controllable device 102 as discussed in detail above with respect to FIG. 2.

As discussed above, in one implementation, the memory 108' stores the user identification data uniquely associated with the PIOT device 220 identifying a user among a plurality of users of the PIOT device 220. Also discussed above, in one implementation, the memory 108' also stores a plurality of hierarchical classes of user(s) as member(s) with each class having permissions to use one or more control instructions among the plurality of control instructions. In one implementation, the data communication receiver 209 receives a user identification data of the PIOT device 220, e.g. from the user's personalized neural device 104 or the user's mobile device. As discussed above, the processor 110' utilizes the received user identification data to search the memory 108' to identify the user among the plurality of users and the corresponding hierarchy class of the identified user for a user-group/class of which the user is the member. The processor 110' transmits the control data signal to the controller 112 that relates to the one or more control instructions permitted for the corresponding hierarchy class.

As discussed above, in one implementation, the data communication receiver 209' receives identifying data from the controller 112. Also, as discussed above, the identifying data includes or allows lookup of controller related information, such as but not limited to location of the controller in the area and/or premises, communication capabilities of the controller, control operations supported by the controller, types of controllable devices controlled by the controller, controller variables for each type of controllable device, or combinations thereof.

As discussed above, in one implementation, the processor 110', in this example in the PIOT device 220, determines a communication capability among the plurality of communication capabilities of the controller based on the identifying data. The processor 110' functions to adapt at least one aspect of the control data signal based on the determined communication capability of the controller 112. Also, as discussed above, in another implementation, the processor 110' determines a type of the controllable device 102 among the plurality of types of controllable devices based on the identifying data. In one implementation, the processor 110' adapts the control data signal to the determined type of the controllable device 102.

As discussed above, in one implementation, the processor 110', in this example in the PIOT device 220, retrieves data identifying control operations supported by the controller based on the identifying data from the controller 112. The processor 110' operates the transmitter 207' to send the data identifying control operations to an output device (e.g., having the display device 312, audio device 314 and/or haptic device 316) of the user via wireless transmission and the network 400. In one example, the control instruction corresponds to a user selection of a control operation among the identified control operations supported by the controller 112.

As discussed above, in one implementation, the memory 108', in this example in the PIOT device 220, stores user preference data associated with the user identification data. In one example, the user preference data includes a preferred user selection of one or more control operations among the identified control operations in the identifying data that are supported by controller 112 in the area 101. Also, as discussed above, in one implementation, upon receipt of the identifying data, the processor 110' accesses the memory 108' to retrieve the user preference data for the user associated with the controller 112. The processor 110' operates the transmitter 207' to send the user preference data to an output device (e.g. having the display device 312, audio device 314 and/or the haptic device 316) of the user device via the data communication transmitter 209. In one example the control instruction corresponds to the user preference data including the preferred user selection of the one or more control operations among the identified control operations supported by the controller 112.

FIG. 5 is a flowchart illustrating an example method 500 for system level neural responsive control of a controllable device configured to provide a premises related service in an area 101 including a premises related service of a system of FIG. 1. In one implementation, the method 500 is provided by the processor 110 of FIG. 1, although a similar method may be implemented in a system like that of FIG. 2.

At block 502, the process involves receiving real-time detected nerve signals (e.g. actual nerve sensor output signals or more often digital data from A/D conversion of the signals from the nerve sensors). The-time detected nerve signals in this example are received from a neural device in an area including a premises related service provided by a controllable device. As discussed above, in one example, the neural device is configured to be positioned on some part of the human body, for example, as a glove to be worn on a person's hand or as a cuff to be worn on person's wrist or forearm. The real-time detected nerve signals are signals detected in real-time from a nervous system of the part of the body such as finger, back, hand, forearm etc. on which the neural device is positioned.

At block 504, the process involves analyzing the real-time detected nerve signals to determine whether the real-time detected nerve signals correspond to one of a plurality of predetermined sets of nerve signals. As noted earlier, each predetermined set of nerve signals is associated with at least one control instruction among a plurality of control instructions associated with the various predetermined signal sets. As discussed above, a control instruction corresponds to controlling the premises related service provided by the controllable device in a particular way. In one implementation, the controllable device includes one of a luminaire or a building automation control (BAC) appliance. Accordingly, each of the control instructions is associated with controlling the premises related service provided by the luminaire or the BAC appliance in a selected manner.

At block 506, the device (e.g. neural device 104 or PIOT device 220 that implements the analysis) generates a control data signal based on the one control instruction, responsive to the determination of correspondence between the real-time detected nerve signals and the one predetermined set of nerve signals. As discussed above, the control instruction is converted into a control data signal, which indicates an intended action related to controlling premises related service in the area. At block 508, the relevant device transmits the control data signal to a controller to control a premises related service provided by the controllable device in the area in response to the control data signal. As discussed above, in one implementation, one of the luminaire or the BAC appliance is selected based on the control instruction and the associated control data signal is generated for transmission to the selected one of the luminaire or the BAC appliance to implement the action corresponding to the instruction that is associated with the predetermined set of nerve signals (which was found to correspond to the detected nerve signals).

FIG. 5A illustrates another flowchart example of a method 520 for system level neural responsive control of a controllable device configured to provide a premises related service in an area 101 including a premises related service of a system of FIG. 1. In one implementation, the method 520 is provided by the processor 110 of FIG. 1, although a similar method may be implemented in a system like that of FIG. 2.

At block 522, the neural device 104 (or PIOT device 220) receives identifying data supported of a controller. At block 524, the relevant device determines a communication capability among a plurality of communication capabilities of the controller, either from the identifying data or by performing a lookup based on the identifying data. At block 526, the device receives real-time detected nerve signals from the nerve sensors, while the neural device is worn by a user in an area offering a premises related service provided by a controllable device. At block 528, a processor of the neural device 104 or the PIOT device 220) analyzes the real-time detected signal to determine that the real-time detected nerve signals are associated with a control instruction among a plurality of control instructions corresponding to the determined communication capability of the controller. At block 530, the processing generates a control data signal based on the control instruction corresponding to the determined communication capability of the controller.

Figure 5B:
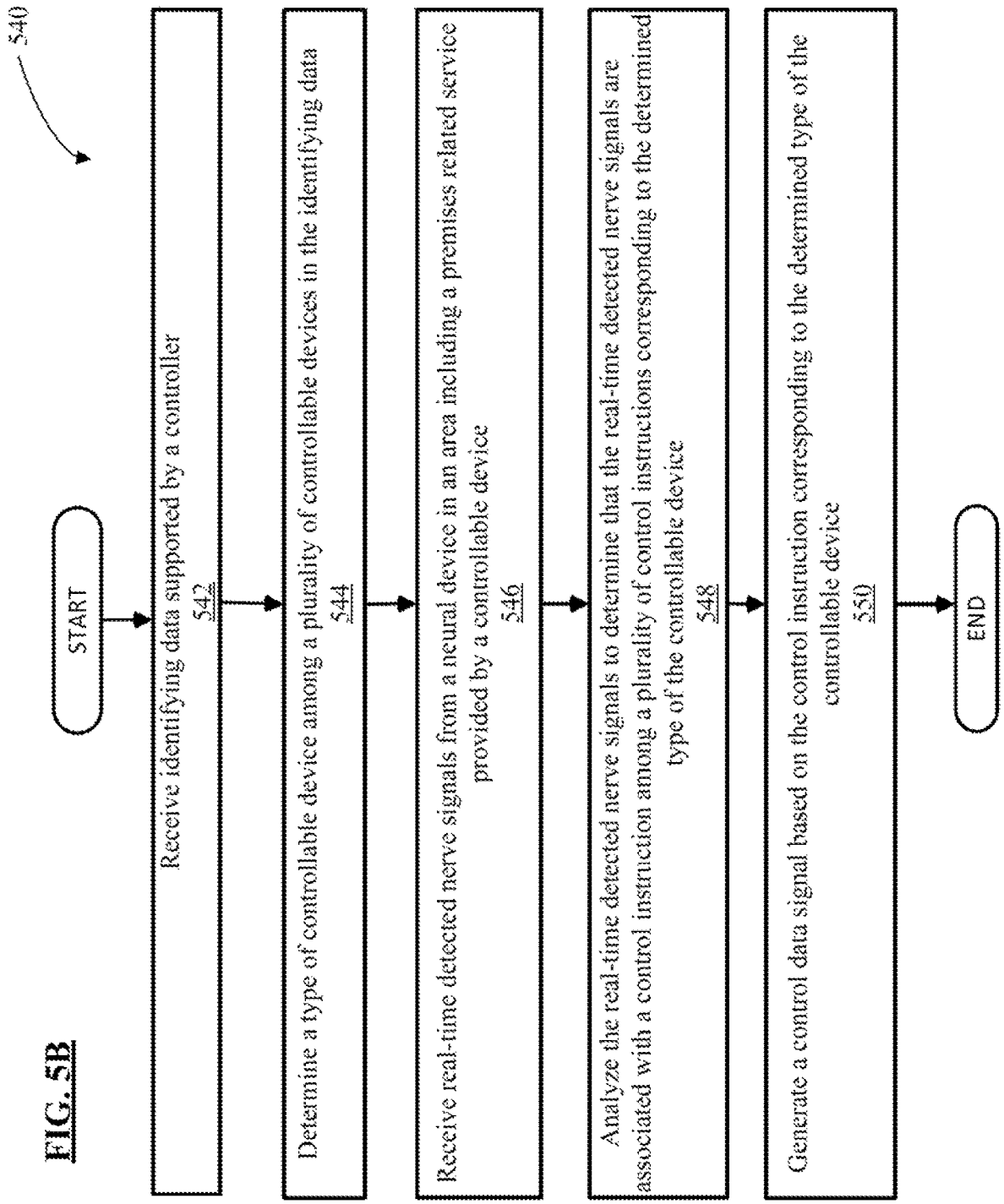
FIG. 5B is an another example flowchart illustrating a method for system level neural sensing control of the premises related service provided by a controllable device in an area of a premises.

FIG. 5B is a flowchart illustrating another example method 540 for system level neural responsive for system level control of a controllable device configured to provide a premises related service in an area 101 including a premises related service of a system of FIG. 1. In one implementation, the method 540 is provided by the processor 110 of FIG. 1, although a similar method may be implemented in a system like that of FIG. 2.

At block 542, a device (e.g. neural device 104 or PIOT device 220 that implements the analysis, etc.) receives identifying data supported by a controller. At block 544, the device determines a type of controllable device among a plurality of controllable devices identified in the identifying data or from a lookup based on the identifying data. At block 546, the device receives real-time detected nerve signals from nerve sensors, while the neural device is worn by a user in an area including a premises related service provided by a controllable device. At block 548, the receiving device analyzes the real-time detected nerve signals to determine that the real-time detected nerve signals are associated with a control instruction among a plurality of control instructions corresponding to the determined type of controllable device. At block 550, that device generates a control data signal based on the control instruction corresponding to the determined type of controllable device.

FIG. 5C is a flowchart illustrating a further example method 560 for system neural level control of a controllable device configured to provide a premises related service in an area 101 including a premises related service of a system of FIG. 1. In one implementation, the method 560 is provided by the processor 110 of FIG. 1, although a similar method may be implemented in a system like that of FIG. 2.

At block 562, a device (e.g. neural device 104 or PIOT device 220 that implements the analysis, etc.) receives identifying data for a controller. At block 564, that device retrieves data identifying control operations supported by the controller based on the identifying data. At block 566, the receives the real time detected nerve signals from nerve sensors, while the neural device is worn by a user in an area including a premises related service provided by a controllable device. At block 568, the receiving device analyzes the real-time detected nerve signals to determine that the real-time detected nerve signals are associated with a control instruction corresponding to a user selection of a control operation among the control operations supported by the controller. At block 570, that device generates a control data signal based on the control instruction corresponding to the user selection of the control operation.

Figure 6:
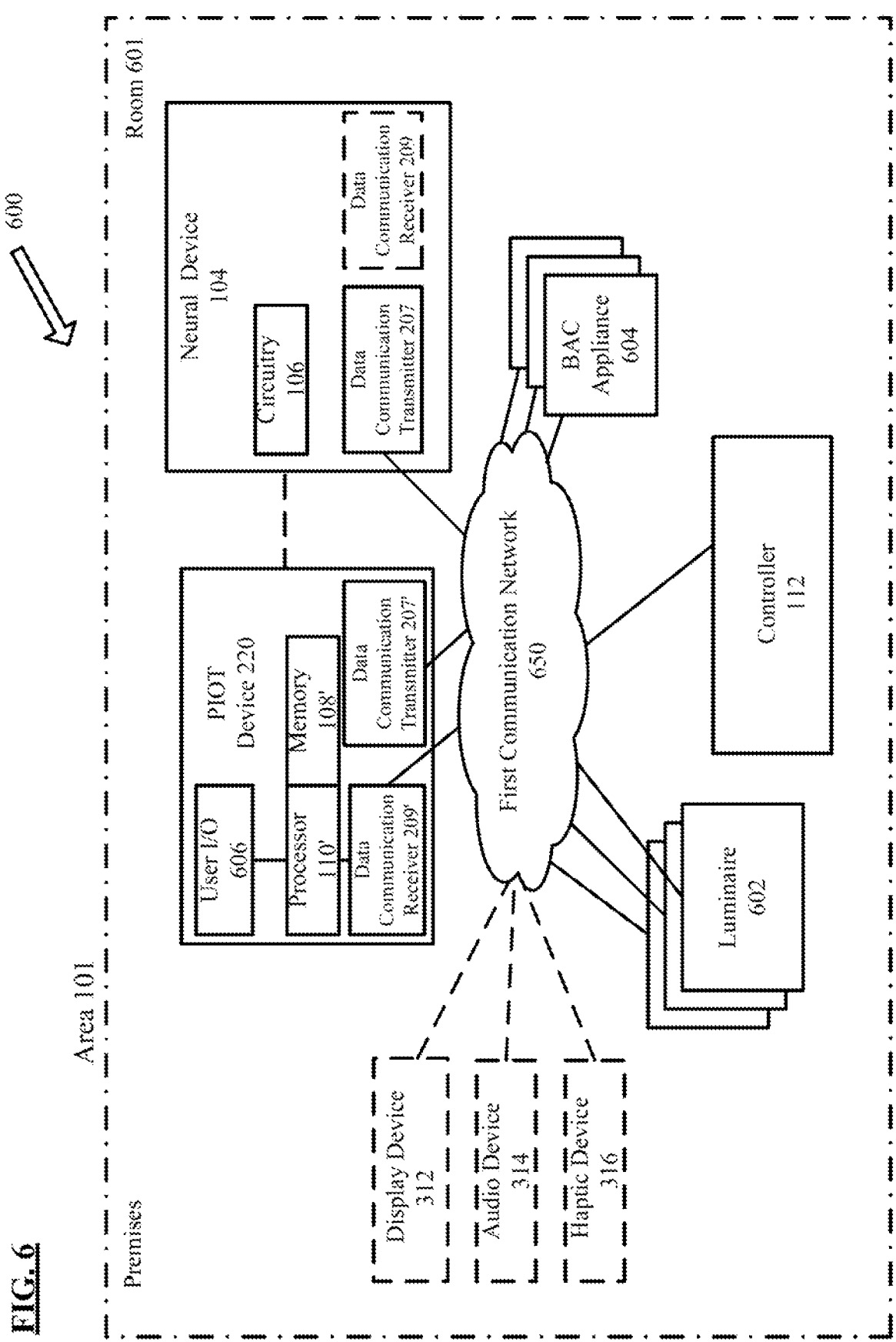
FIG. 6 is a functional block diagram of an example of a system of lighting related equipment and building automation control (BAC) capable appliances as well as one or more elements that may offer neural responsive control of the lighting related equipment and the BAC capable appliance.

As discussed above, the controllable device 102 provides a premises related service in an area 101 of a premises. The controllable device 102 may be one or more luminaires, various BAC appliances etc. FIG. 6 illustrates an example of a system 600 serving an area 101 of the premises represented by a room 601. The room 601 includes one or more luminaires 602 and one or more BAC appliances 604 as examples of different types of controllable devices 102. Each luminaire 602 is configured to provide a desired level of lighting for the intended use of the particular space in the room 601. A BAC appliance 604 may be configured, for instance, to regulate the temperature in the room 601 or to control access to the room 601, etc. Although, FIG. 6 illustrates providing lighting control and building management services in the room 601, it should be apparent that such services may be provided in a similar manner in other rooms and/or other types of services areas within or about a particular area of the premises such as in a building or indoors and outdoors about a campus or the like. Also, even though, a plurality of luminaires 604 and a plurality of BAC appliances 602 are illustrated in the room 601, it should be apparent that the room 600 may include only on luminaire 602 or only one BAC appliance 604.

A controller 112 is configured to control the premises related services in the room 601. In one implementation, control related operations of such premises related services include, for example, lighting operations of the system, such as occupancy sensing, ambient light level or color characteristics of light sensing in the area or level or color of light emitted from the luminaire 602 serving the particular portion of the area and corresponding responsive control of the luminaire(s) 602. In another implementation, where the premises related services include operations of the system or for more general communication about sensing and/or control of conditions in the area 101 for still further purposes. Examples of other sensed and/or controllable conditions include temperature or humidity for HVAC control, vibration for reporting of earthquakes or similar events, fire, smoke or gas detection, sound for user input or for detection of breakage or the like, as well as window or door state for security or access control. Other examples of operations include power monitoring, an object/occupant identification, etc.

In one implementation, the room 601 includes the controller 112 as a separate standalone system component. For example, the controller 112 may take the form of a wall controller for lighting or a thermostat for HVAC control. Alternatively, the controller 112 may be included in a luminaire 602 or a BAC appliance 604. In other implementations, the controller 112 may be in a different location at the premises rather than actually within the room 601.

In one implementation, the controller 112 is coupled to communicate with the controllable device 102 such as the luminaire(s) 602 and/or the BAC appliance(s) 604 in the room 601 via a first communication network 650 such as optical, radio frequency wireless or wired communication network. In one example, the premises related service are light related operations. The controller 112 is configured to control the light related operations associated with the luminaire(s) 602. In addition or as an alternative example, the premises related service may include building management functions. In such an example, the controller 112 is configured to control the building management functions associated with the BAC appliance(s) 604 serving the room 601.

In one implementation, a user (not shown) with neural device 104 including the circuitry 106 and the data communication transmitter 207 (and optionally, the data communication receiver 209) is configured to be positioned on a head of the user while the user is in the room 601. In one example, sensors of the neural device 104 detect nerve signals from the nervous system of the part of the body of the user in real time, and those signals are processed by the circuitry 106. Digitized data of the detected nerve signals is transmitted by the data communication transmitter 207 to the PIOT device 220 of the user.

The data communication receiver 209' of the PIOT device 220 receives the digitized real-time detected nerve signals. In one implementation, the neural device 102 and the PIOT device 220 communicate with each other via the first communication network 650. In an alternate implementation, the neural device 102 and the PIOT device 220 directly communicate with each other, for example, via a wire or fiber link or via a wireless technology different from that utilized to access the network 650. In another alternate implementation, the PIOT device 220 is coupled to communicate with one or more of the user devices (e.g. display device 312, audio device 314 and haptic device 316). The PIOT device 220, in the example, also includes a wireless data communication transmitter as shown at 207', for communications via the network 650, e.g. with the controller 112.

In one implementation, the processor 110' utilizes the instructions in the memory 108' to execute functions such as determine a correspondence between the real-time detected nerve signals and one pre-determined set of nerve signals for which reference data is stored in the memory 108' and generate a control data signal based on at least one control instruction among a plurality of control instructions that corresponds to the one pre-determined set of nerve signals. The data communication transmitter 209' wirelessly transmits the control data signal to the first communication network 650, and through the network 650, to the controller 112 to control the premises related service provided by one of the luminaire 602 and/or the BAC appliance 604 in the room.

In the example, the PIOT device 220 (or possibly the neural device 104) includes a user interface (UI) for output to the user, such as the display device 312, audio device 314 or the haptic device 316. Some input examples of the UI 606 include a toggle switch, one or more push button switches, a rotary controller, one or more sliders, a keypad, various indicator lights, haptic feedback components, and/or a touchscreen display. Other examples of the UI input include a video input and associated processing for gestural control detection, a microphone, an occupancy/motion sensor, proximity sensor, etc. Although not shown, each of the system elements that uses power to operate as described will include a power supply circuit and will connect to or possibly contain a power source.

Although the neural device, PIOT device and any optional output devices for providing feedback or other information to the user may be separated, in most examples, such devices will be carried or worn by the user at any one time, whether on or off of the premises where the controllable device is located.

Figure 6A:
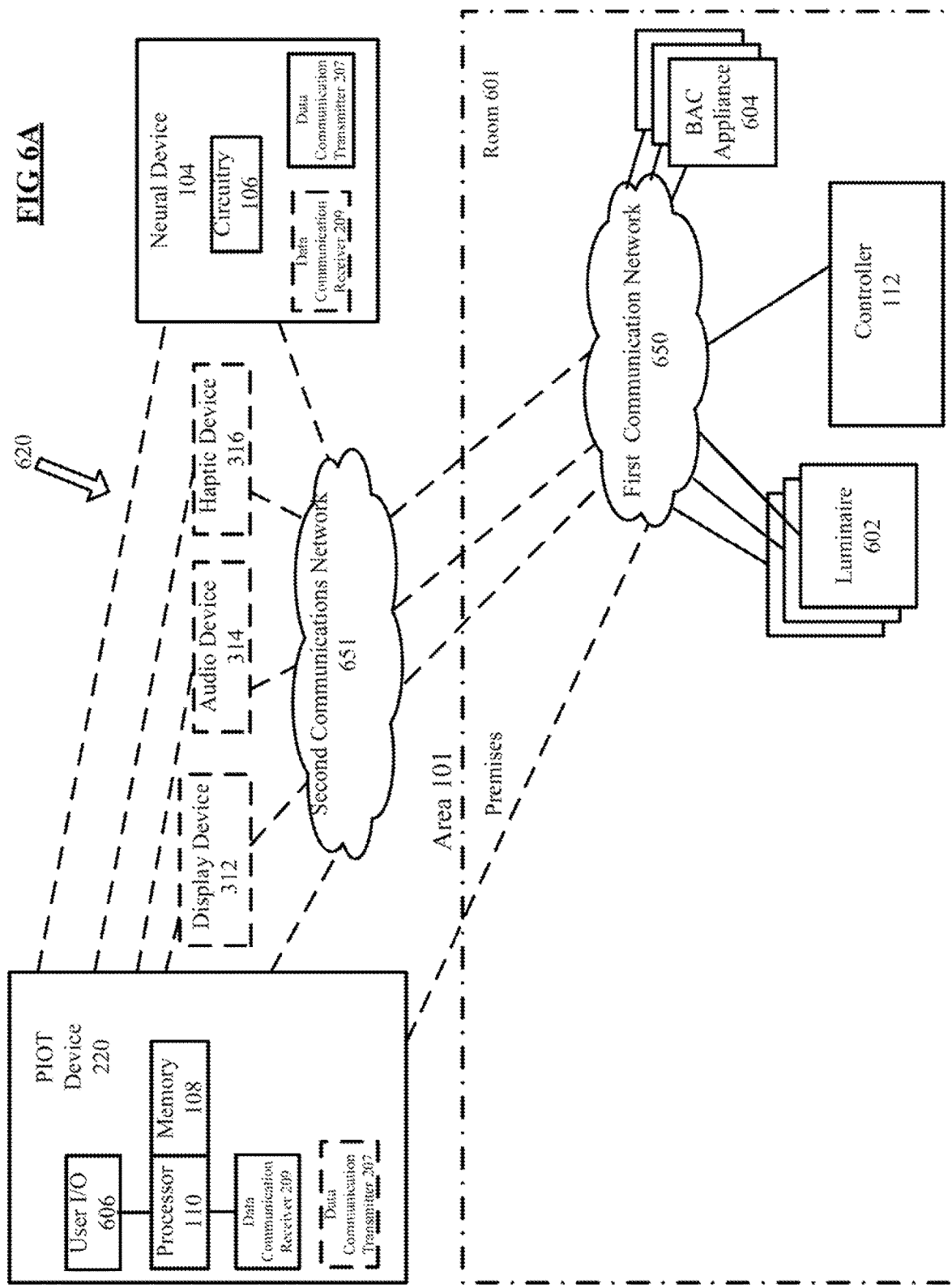
FIG. 6A is a functional block diagram of another example of lighting related equipment and building automation control (BAC) capable appliances as well as one or more elements that may offer neural responsive control of the lighting related equipment and the BAC capable appliance.

FIG. 6A illustrates another example of a system 620 serving the area 101 of the premises represented by the room 601. The system 620 functions similar to the system 600 discussed above except the neural device 104 and the PIOT device 220 are located outside the area 101 such that the nerve signals are detected by the neural device 104 outside of the premises of the room 601, which are then processed by the circuitry 106 and transmitted by the data communication transmitter 207 to the PIOT device 220. The PIOT device 220 is shown by way of example outside of the premises and/or possibly outside of the room 601, e.g. where the neural device 104 and the PIOT device 220 are worn and/or carried by the user. The PIOT device 220, however, may be inside the room and/or the premises (e.g. at the same or another location as the neural device 104). In one example, the user device, for example hosting the display device 312, the audio device 314 and/or the haptic device 316, also is located outside the premises of the room 601, e.g. with the user wearing the neural device 104; and the neural device 104 and the PIOT device 220 device communicate with each other and with such a user device via a second communication network 651 such as an optical, RF wireless or a wired communication network.

Figure 6B:
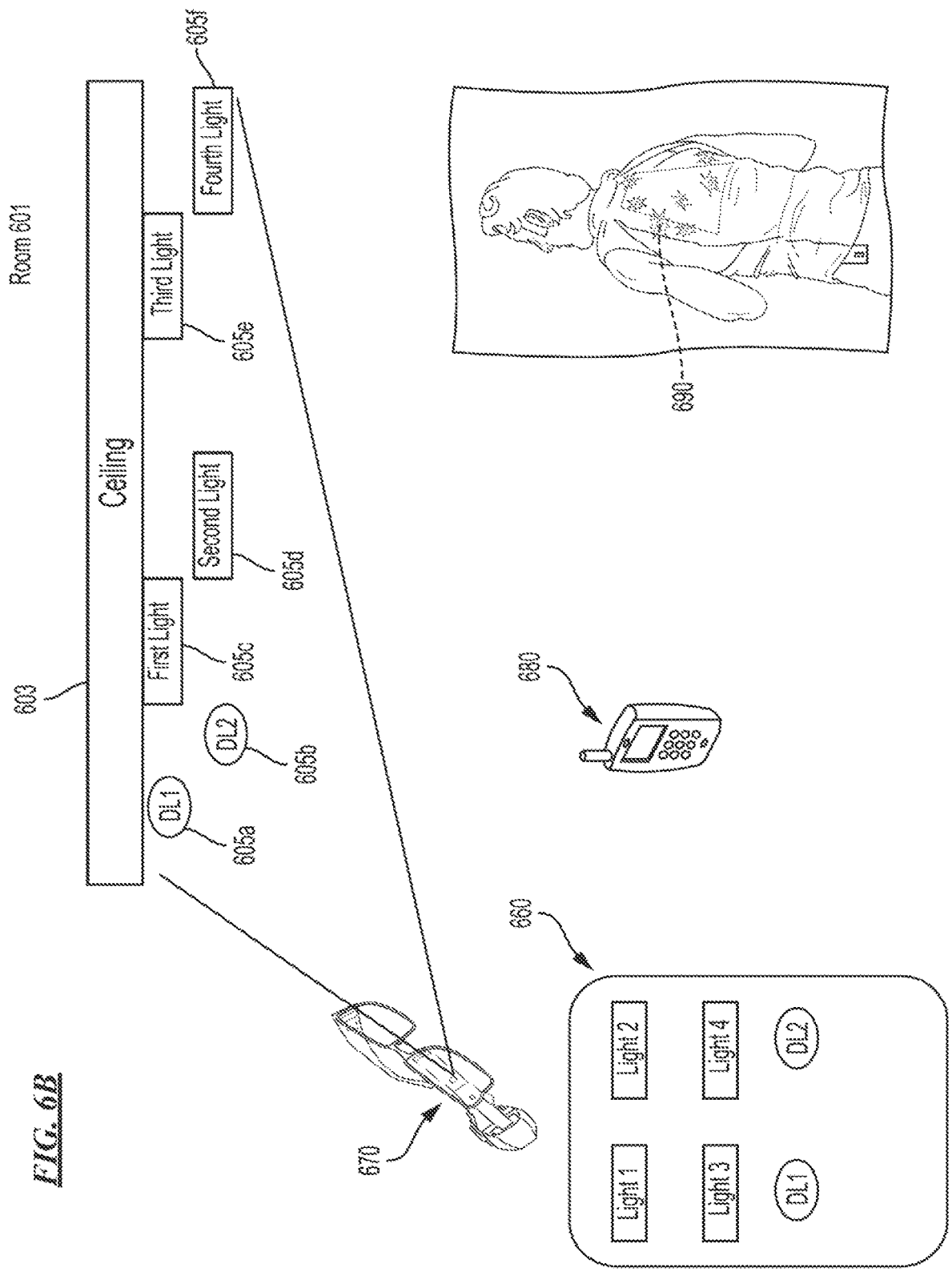
FIG. 6B illustrates an example of providing data associated with the lighting devices in the area.

FIG. 6B illustrates an example of providing data associated with several lighting devices (as the controllable device(s) 102) in the room 601. Also, shown is a ceiling 603 in the room 601 and luminaires or the like labeled as "lights" for convenience in the drawing. In one example, there are illustrated six lighting devices, including a first ($1^{st}$) downlight (DL1) 605a, a second ($2^{nd}$) downlight (DL2) 605b, and four other lights shown as a first light 605c, a second light 605d, a third light 605e, and a fourth light 605f. In one example, the four lights 605c-605f are mounted on or hung below the ceiling 603. In one example, the two downlights, 605a and 605b are downlight type fixtures that may be recessed into, mounted or hung below the ceiling 603. Although the light sources are illustrated to be located on the ceiling 603, it should be apparent that the light sources may be located either on a wall or floor or combinations thereof in the room 601. Also, in the example, six lighting devices are shown, it is known to one of ordinary skill in the art that less than or more than six lighting devices may be provided in the room 601. The lighting devices may include but not limited to light emitting diodes (LEDs), fluorescent lamps, halogen lamps, metal halide lamps, high intensity discharge lamps or like.

In one implementation, the data associated with the six lighting devices is provided to the user via one of the user devices such as the display device 312, audio device 314 and the haptic device 316. In one example, the data is provided to the user upon request from the user when the user enters the room 601. In another example, the data is automatically provided to the user when the user enters the room 601. In one example, the display device 312 is a smart mobile phone or the like 680; and the data may be displayed on a screen of the mobile device 680 as shown.

In another example, the display device is an display incorporated in a head gear 670 including a camera (not shown); and the data may be displayed to the user who wears the head gear 670. In one example, the head gear 670 is a set of augmented reality (AR) glasses, which includes additional hardware such as an optical sensor/camera (not shown) to track the eyeball of the wearer of the AR glasses and estimates gaze so that neural/nerve commands to control the lights can be directed to specific lights being directly observed by the wearer of the AR glasses. Other administrator level functions such as grouping lights can also be performed, highly augmented by the visual feedback to the AR glasses.

In one example, the audio device 314 is a standard phone 680 and the data is provided to the user via audio on the standard phone 680. In one example, the haptic device 316 is a wearable device 690, which provides for a physical contact between the user and a computer such as the user will receive the data via felt sensation on some part of the body. In one example, upon user selection of the data (associated with the lighting devices as shown) as provided to the user, user selections are collected and stored as the user preference data. As discussed above, the user preference data is a preferred user selection of one or more control operations among the identified control operations of the controllable device 102 supported by the controllable 112.

Figure 7:
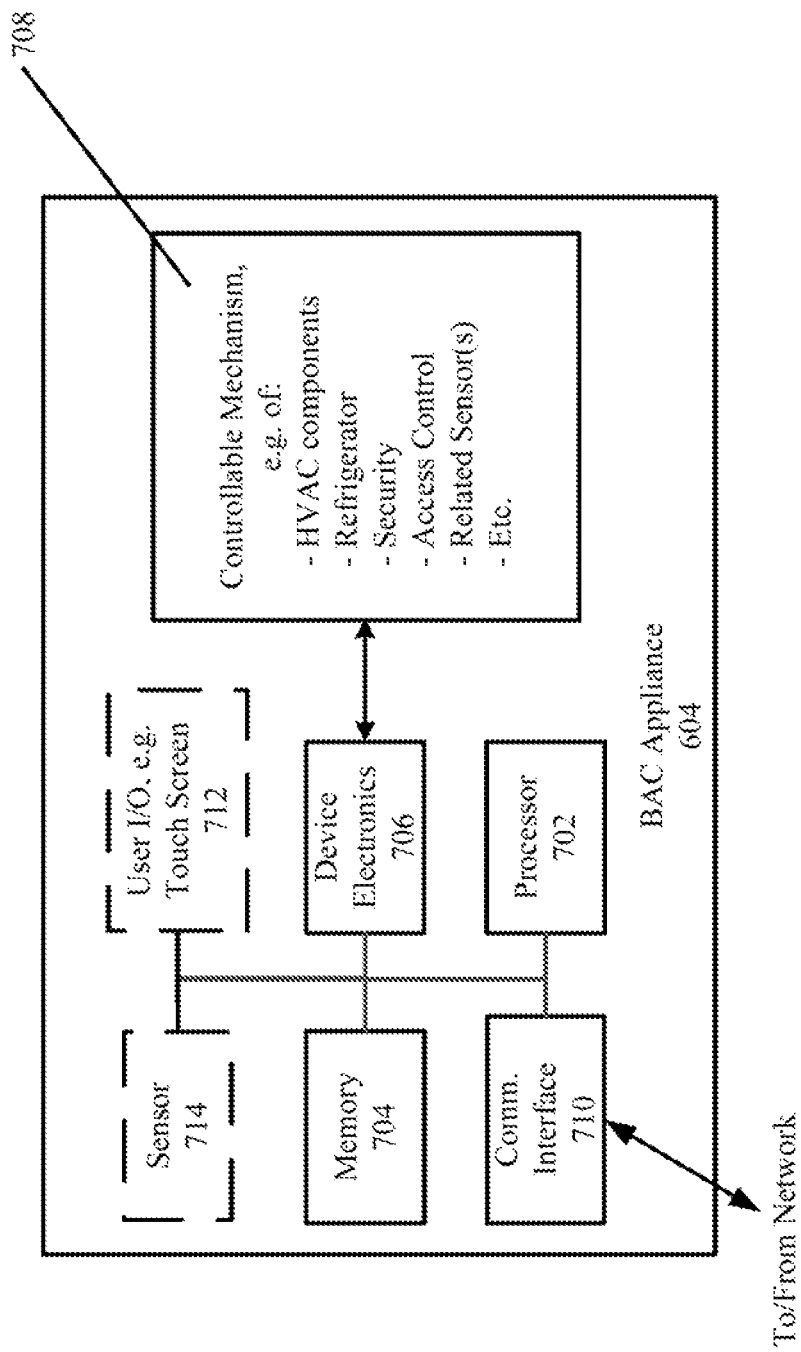
FIG. 7 is a functional block diagram of an example of an intelligent building automation control (BAC) capable appliance for use in a system like one of the systems shown for example in FIG. 6 and FIG. 6A.

FIG. 7 is a functional block diagram illustrating an example of an intelligent building management element, such as the BAC appliances 604 for use in a system like that of FIG. 6. The BAC appliance 604 (FIG. 7) is an intelligent device in that the BAC appliance 604 includes a processor 702 and a memory 704 and program in the memory 704 for execution by the processor 702 to implement the intended functions of the BAC appliance 604. This 'brain' of the BAC appliance 604 will be coupled to and control appropriate device drive electronics 706. The drive electronics 706 provides an interface to a controllable mechanism 708 of the particular BAC appliance 604, to allow the processor 702 to control the mechanism 708, or to receive sensor data from the mechanism or both. The drive electronics 706 and the programming (e.g. stored in memory 704) that is run by the processor 702 to control operation of each particular BAC appliance 604 will depend on the particular type device used as the mechanism 708 and thus on the particular type of building management BAC appliance product it represents or implements.

The examples of the BAC appliance 604 may be virtually any type of device, which may utilize data communications, in this case, via the elements and network of the system 600 of FIG. 6. By way of a few examples, the controllable mechanism 708 may be any of a variety of HVAC components (e.g., elements of a thermostat, one or more elements of the heat/cooling system, controllable vents or dampers within the duct work), one or more cooling or other elements of a refrigerator, any of a variety of components of a security system, any of a variety of access control elements, and/or sensors related to any or all of the above functions. The BAC appliance 604 also includes a communication interface 710. Similar to the communication interfaces in the other intelligent system elements (FIG. 6), the interface 710 connects or otherwise couples to the network in the service area and supports two-way data communication through the first communication network 650, for example, with the controller 112.

In the example of FIG. 7, although the BAC appliance 604 is shown as having one processor 702, it is known to one of ordinary skill in the art that the BAC appliance 604 may include multiple processors. For example, a particular configuration for a BAC appliance 604 may utilize a multi-core processor architecture. Also, some of the other components, such as the communications interfaces, may themselves include processors. Alternatively, the BAC appliance 604 may use a Micro-Control Unit (MCU), which is a microchip device (e.g. small computer or computer like device formed on a single chip) that incorporates a processor serving as the programmable central processing unit (CPU) as well as one or more of memories 704 and possibly other elements of the appliance 604 such as the communication interface 710.

The BAC appliance 604 may include one or more input and/or output (I/O) elements 712 for a user interface (instead of or in addition to the mechanism 708). The user I/O element 712, for example, may include a toggle switch, a rotary controller, one or more sliders, a keypad and/or a touchscreen display. The precise user I/O element, if provided, depends on the operational characteristics of the particular BAC appliance 604. For example, for an HVAC controller, the user I/O element(s) 712 might be similar to those of a digital thermostat. A touchscreen display, as another example, may support touch and touch gesture input as well as visual display output. Other examples of the UI input may include a video input and associated processing for gestural control detection, a microphone, an occupancy/motion sensor, proximity sensor, etc. If provided, outputs may be visual, audible, tactile, etc. For example, a microphone and/or speaker may be used to support audible input and/or output, whereas a camera in combination with projector or display may be used to support visual input and/or output.

As an alternative or in addition to any sensors included in the controllable mechanism 708, the BAC appliance 604 may include one or more sensors 714 (instead of or in addition to the mechanism 708). If included, the type of sensor 714 in a particular BAC appliance 604 would depend on the type of element and/or the mechanism 708 that the 'brain' controls either within the appliance itself or in same or another appliance via a BMS application stored in the memory 704.

Figure 8:
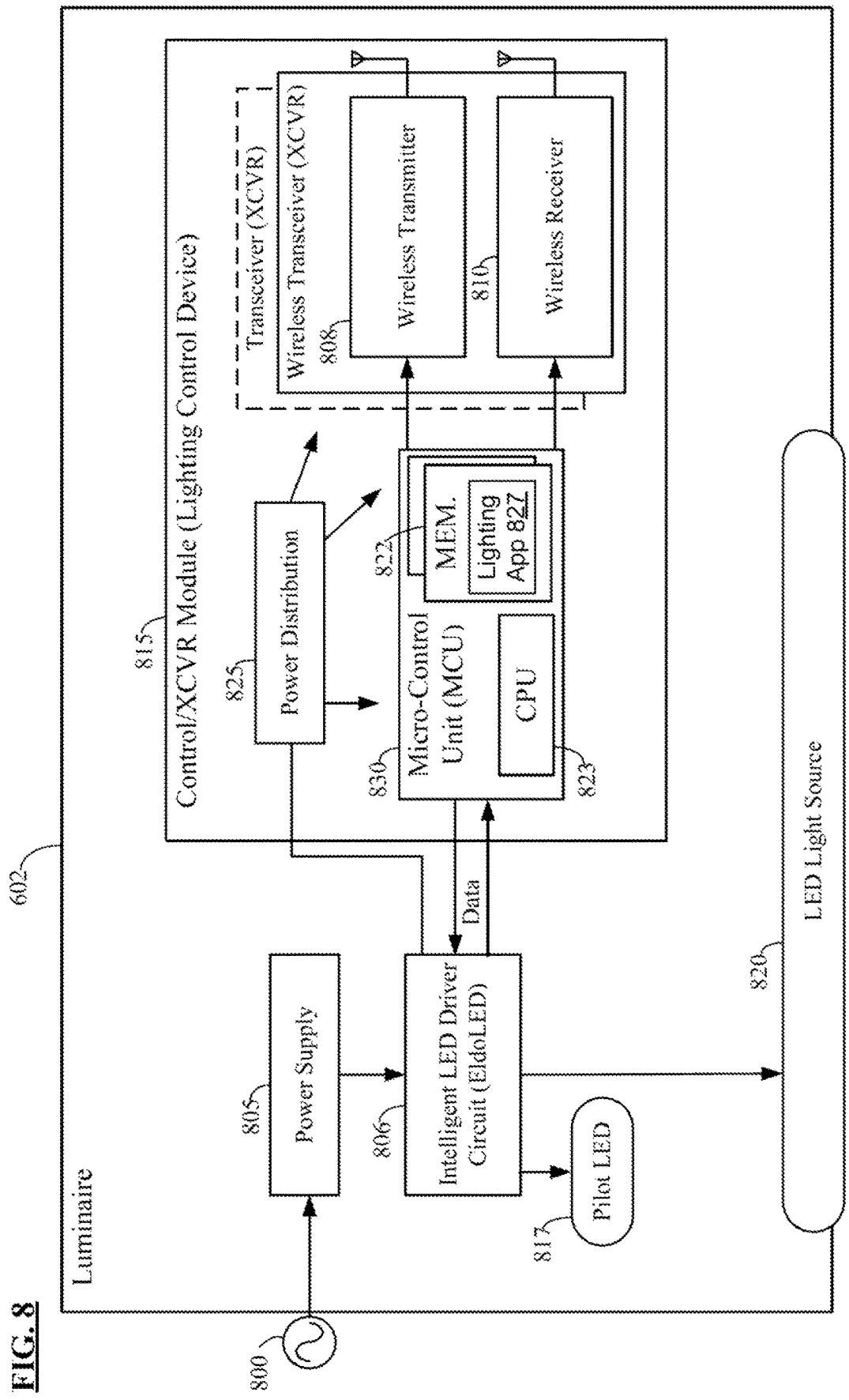
FIG. 8 is a functional block diagram of an example of an intelligent luminaire for use in a system like one of the systems shown for example in FIG. 6 and FIG. 6A.

FIG. 8 is a functional block diagram illustrating an example of an intelligent luminaire, such as the luminaire 602 for use in a system like that of FIG. 6. Luminaire 804 is an integrated light fixture that generally includes a power supply 805 driven by a power source 800. Power supply 805 receives power from the power source 800, such as an AC mains driven supply circuit, a battery, a circuit connected to solar panel, or any other AC or DC source. Power supply 805 may include a magnetic transformer, electronic transformer, switching converter, rectifier, or any other similar type of circuit to convert an input power signal into a power signal suitable for luminaire 804.

The example luminaire 602 includes a control/XCVR module 815. Although other types of luminaires may be utilized and thus controlled as described herein, the example luminaire 804 is LED-based type of lighting device Luminaire 804 therefore further includes an intelligent LED driver circuit 806 coupled to the control/XCVR module 815 and a light emitting diode (LED) light source 820. Intelligent LED driver circuit 806 is coupled to LED light source 820 and drives that LED light source 820 by regulating the power to the one or more LEDs of the light source 820 by providing a constant quantity or power to LED light source 320 as its electrical properties change with temperature, for example. The intelligent LED driver circuit 806 includes a driver circuit that provides power to LED light source 820 and a pilot LED 817. The pilot LED 817 may be included as part of the control/XCVR module 315. Intelligent LED driver circuit 806 may be a constant-voltage driver, constant-current driver, or AC LED driver type circuit that provides dimming through a pulse width modulation circuit and may have many channels for separate control of different LEDs or LED arrays. An example of a commercially available intelligent LED driver, circuit 806 is manufactured by EldoLED. LED driver circuit 806 can further include an AC or DC current source or voltage source, a regulator, an amplifier (such as a linear amplifier or switching amplifier), a buck, boost, or buck/boost converter, or any other similar type of circuit or component. LED driver circuit 806 outputs a variable voltage or current to the LED light source 820 that may include a DC offset, such that its average value is nonzero, and/or an AC voltage.

Control/XCR module 815 includes power distribution circuitry 825 and a micro-control unit (MCU) 830. As shown, MCU 830 is coupled to LED driver circuit 806 and controls the light source operation of the LED light source 820. MCU 830 includes a memory 322 (volatile and non-volatile) and a central processing unit (CPU) 823. The memory 822 includes a lighting application 827 (which can be firmware) for both occupancy sensing/counting and lighting control operations. The power distribution circuitry 825 distributes power and ground voltages to the MCU 830, wireless transmitter 808 and wireless receiver 810, to provide reliable operation of the various circuitry on the sensor/processing circuitry 815 chip.

Luminaire 804 also includes a wireless radio communication interface system configured for two way wireless communication on at least one band. Optionally, the wireless radio communication interface system may be a dual-band system. It should be understood that "dual-band" means communications over two different (possibly separate or partially overlapping) RF bands. The communication over the two RF bands can occur simultaneously (concurrently); however, it should be understood that the communication over the two separate RF bands may not actually occur simultaneously.

In our example, the luminaire 804 has a radio set that includes radio transmitter 808 as well as a radio receiver 810, together forming a radio transceiver. The wireless transmitter 808 transmits RF signals on a lighting control network, such as the first communication network 650 of FIG. 6. This wireless transmitter 808 supports wireless communication of control and systems operations information, during luminaire operation and during transmission over the first wireless communication band. The wireless receiver carries out receiving of the RF signals from other system elements on the network and generating RSSI data based on signal strengths of the received RF signals.

If provided (optional) another transceiver (Tx and Rx) may be provided, for example, for point-to-point communication, over a second different wireless communication bands, e.g. for communication of information other than the control and systems operations information, concurrently with at least some communications over the first wireless communication band. Optionally, the luminaire 804 may have a radio set forming a second transceiver (shown in dotted lines, transmitter and receiver not separately shown). The included transceiver (solid lines), for example, may be a sub GHz transceiver or a Bluetooth transceiver configured to operate in a standard GHz band. A dual-band implementation might include two transceivers for different bands, e.g. for a sub GHz band and a GHz band for Bluetooth, and Bluetooth band and a WiFi band, or the like. Additional transceivers may be provided. The particular bands/transceivers are described here by way of non-limiting example, only. If two bands are supported, the two bands may be for different applications, e.g. lighting and/or BAC control system operational communications and system element maintenance/commissioning. Alternatively, the two bands may support traffic segregation, e.g. one band may be allocated to communications of the entity owning/operating the system at the premises whereas the other band may be allocated to communications of a different entity such as the system manufacturer or a maintenance service bureau.

The MCU 830 may be a system on a chip (SoC) that includes the CPU 823, memory 823, interface ports (not shown), etc. Alternatively, a system on a chip may include the transmitter 808 and receiver 810 as well as the circuitry of the MCU 830.

As shown, the MCU 830 includes programming in the memory 822. A portion of the programming configures the CPU (processor) 823 to control the LED light source 820 via the driver circuit 806 and/or to determine occupancy sensing/counting via analysis of characteristics of RF signals in the vicinity or responsive to a sensor (not shown), in an area served by the lighting network, including the communications over one or more wireless communication bands/networks. The programming in the memory 822 includes a real-time operating system (RTOS) and further includes a lighting application 827 which is firmware/software for controlling of the light source and engages in any related that communications with other devices on the system/network, for example, controlling the light source based on occupancy sensing/counting determined by the CPU 823 of this or another luminaire. The lighting application 827 programming in the memory 822 carries out lighting control operations in the area. The programming for the determination of an occupancy and/or occupancy count in the area and/or lighting control may be implemented as part of the RTOS, as part of the lighting application 827, as a standalone application program, or as other instructions in the memory.

As shown by the above discussion, some of the functions relating to the neural responsive control of the luminaire or the building management appliances may be implemented on computers connected for data communication via the components of a communication network, operating as one or more network connected hardware elements in the wireless communication network as shown in FIG. 6. Although special purpose devices may be used, such computer devices also may be implemented using one or more hardware platforms intended to represent a general class of data processing device, albeit with an appropriate network connection for data communication.

As known in the data processing and communications arts, a general-purpose computer typically comprises a central processor or other processing device, an internal communication bus, various types of memory or storage media (RAM, ROM, EEPROM, cache memory, disk drives etc.) for code and data storage, and one or more network interface cards or ports for communication purposes. The lighting control and building management control functionalities involve programming, including executable code of the software architecture, as well as associated stored data, e.g. the files or other data used or processed during execution of the software architecture. The programming code is executable by the general-purpose computer that functions as an actual or physical gateway device and/or one or more general-purpose computers that implement the gateway functions in the cloud. In operation, the code is stored within the general-purpose computer platform. At other times, however, the programming and/or any associated files or other data may be stored at other locations and/or transported for loading into the appropriate general-purpose computer system. Execution of such code by a processor of the computer platform enables the platform to implement the methodology or functionalities for the implementation of neural control of the luminaire and the building management appliance, in essentially the manner performed in the implementations discussed and illustrated herein.

Figure 10:
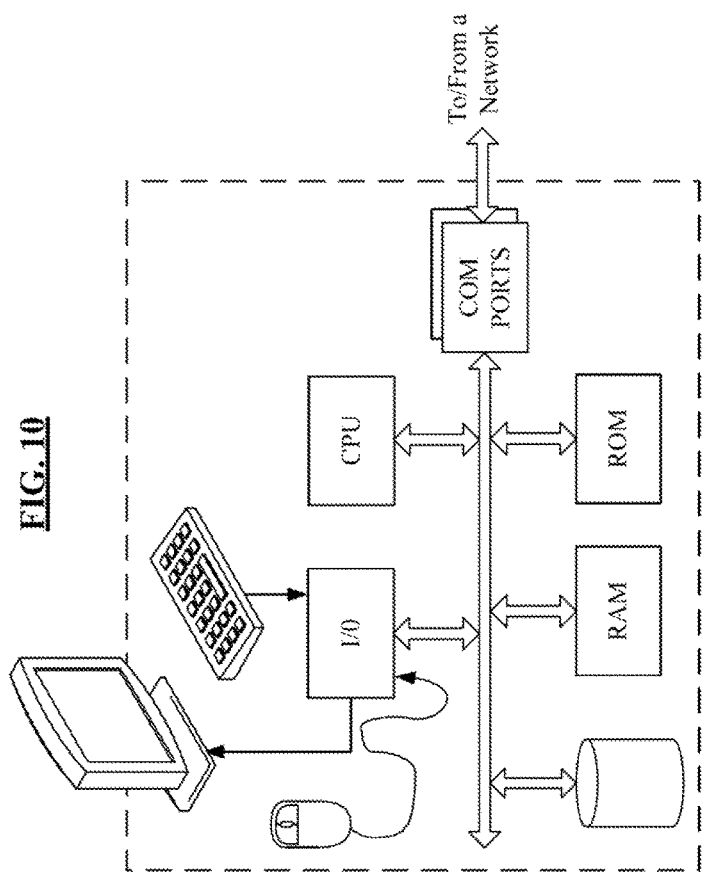
FIG. 10 is a simplified functional block diagram of a personal computer or other work station or terminal device, for possible communication with the gateway or cloud implementation of the control system.
Figure 9:
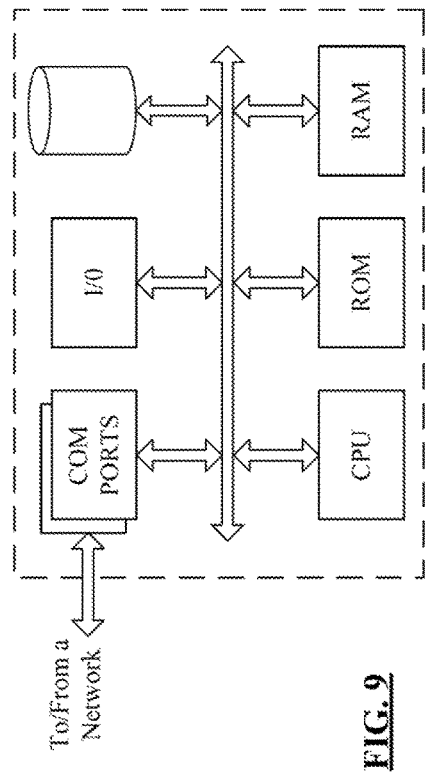
FIG. 9 is a simplified functional block diagram of a computer that may be configured as a host or server, for example, to function as a gateway or as an outside/cloud server in one of the control systems.

FIGS. 9 and 10 provide functional block diagram illustrations of general purpose computer hardware platforms. FIG. 9 illustrates a network or host computer platform, as may typically be used to implement a server, gateway or cloud computing platform. FIG. 10 depicts a computer with user interface elements, as may be used to implement a personal computer or other type of work station or terminal device, although the computer of FIG. 10 may also act as a server, gateway, host computer, etc. if appropriately programmed. It is believed that those skilled in the art are familiar with the structure, programming and general operation of such computer equipment and as a result the drawings should be self-explanatory.

A network computer, for example (FIG. 9), includes a data communication interface for packet data communication. That computer element also includes a central processing unit (CPU), in the form of one or more processors, for executing program instructions. The network computer platform typically includes an internal communication bus, program storage and data storage for various data files to be processed and/or communicated by the server or gateway functions, although the network computer element often receives programming and data via network communications. The hardware elements, operating systems and programming languages of such computers are conventional in nature, and it is presumed that those skilled in the art are adequately familiar therewith. Of course, the functions relating to the neural responsive control of the controllable device, implemented via the software architecture, may be implemented in a distributed fashion on a number of similar network computer hardware platforms, to distribute the processing load and/or offer the gateway functionalities as a cloud service.

Figure 11:
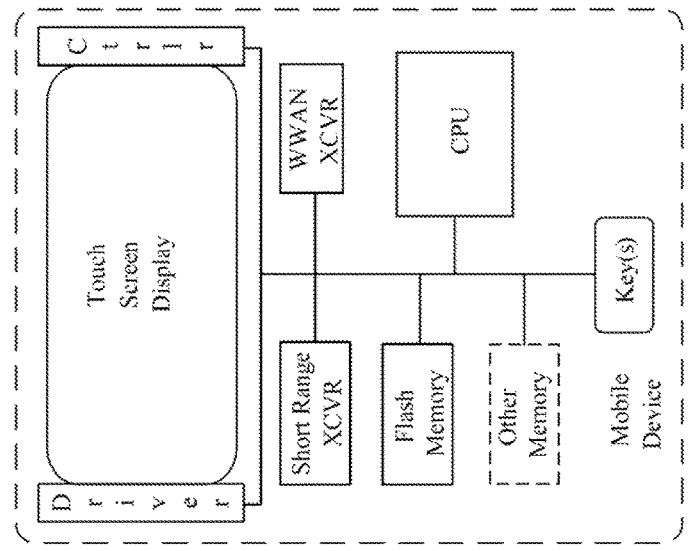
FIG. 11 is a simplified functional block diagram of a mobile device, e.g. smartphone or tablet, as an alternate example of a user terminal device, for possible communication with the gateway or cloud implementation of the control system.

A computer type user terminal device, such as a PC or tablet computer, similarly includes a data communication interface CPU, main memory and one or more mass storage devices for storing user data and the various executable programs (see FIG. 10). A mobile device type user terminal (FIG. 11) may include similar elements, but will typically use smaller components that also require less power, to facilitate implementation in a portable form factor. The various types of user terminal devices will also include various user input and output elements. A computer, for example, may include a keyboard and a cursor control/selection device such as a mouse, trackball, joystick or touchpad; and a display for visual outputs. A microphone and speaker enable audio input and output. Some smartphones include similar but smaller input and output elements. Tablets and other types of smartphones utilize touch sensitive display screens, instead of separate keyboard and cursor control elements. The hardware elements, operating systems and programming languages of such user terminal devices also are conventional in nature, and it is presumed that those skilled in the art are adequately familiar therewith.

Hence, aspects of the functionalities for the neural responsive control of the controllable device outlined above may be embodied in programming for the software architecture (see e.g. neural device 104 of FIGS. 1, 2 and 3, and/or Controller 112 of FIGS. 1 and 2 and/or the PIOT device of FIGS. 2 and 4). Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the programming and/or data. All or portions of such software may at times be communicated through the Internet or various other telecommunication networks. Such communications, for example, may enable loading of the programming and/or relevant data from one computer or processor into another, for example, from a management server or host computer of a manufacturer or control service provider into the computing element that will run the software architecture, such as that of a neural device, a PIOT device or a controller. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution and/or data for relevant processing.

Program instructions may comprise a software or firmware implementation encoded in any desired language. Programming instructions, when embodied in a machine readable medium accessible to a processor of a computer system or other programmable device, render the computer system or device into a special-purpose machine that is customized to perform the operations specified in the program instructions.

The implementations described above and shown in the drawings are given by way of non-limiting examples. Many aspects of the implementations may use other specific components or processing steps.

For example, various types of sensors may be used for EEG detection and/or sensing of nerve signals. EEG equipment uses electrodes on or implanted under the skin to measure voltage fluctuations resulting from ionic current within the neurons of the brain. Nerve signals may be similarly detected on other parts of the body, e.g. the hand, forearm or face, using electrodes in contact with the skin or using implanted electrodes. EEG sensing or neural sensing, however, may be implemented using other sensor technologies. For example, electrical currents such as signals in the brain or nerves also produce magnetic fields that may be detected by appropriately placed magnetic sensors. An all optical implantation of a magnetic sensor, for example, has been recently developed to detect small magnitude magnetic fields for applications such as magnetic resonance imaging and detection of the firing of neurons in the body. The example sensor uses a polymer nanoparticle composite that is sensitive to a magnetic field in combination with an optical fiber. The optical magnetic sensor and other types of sensors may be used in the examples described above.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A personal Internet of Things (PIOT) device comprising:
    a transceiver, including:
        a data communication receiver configured to receive data from a neural device positioned on a part of a body of a user at least while the user is in an area of a premises where a premises related service is provided by a controllable device; and
        a data communication transmitter;
    a processor coupled to the receiver and transmitter;
    a memory accessible by a processor;
    instructions stored in the memory for execution by the processor:
    data stored in the memory associating each of a plurality of predetermined sets of nerve signals detected via the neural device with at least one control instruction among a plurality of control instructions,
    wherein execution of the instructions by the processor configures the PIOT device to:
        receive data regarding nerve signals detected in real-time from the neural device via the data communication receiver;
        using the stored data, analyze the data regarding the real-time detected nerve signals to determine whether the real-time detected nerve signals correspond to one of the plurality of predetermined sets of nerve signals associated with one of the control instructions;
        generate a control data signal based on the one control instruction, responsive to the determination of correspondence between the real-time detected nerve signals and the one predetermined set of nerve signals; and
        via the data communication transmitter, transmit the control data signal to a controller coupled to or in communication with the controllable device to control the premises related service provided by the controllable device in the area.

2. The PIOT device of claim 1, wherein:
    the data communication receiver is configured to receive identifying data from the controller; and
    execution of the instructions by the processor further configures the PIOT device to:
        determine a communication capability of the controller responsive to the identifying data, from among a plurality of communication capabilities supported by the POIT device; and
        adapt at least one aspect of the control data signal to the communication capability of the controller.

3. The PIOT device of claim 1, wherein:
    the data communication receiver is configured to receive identifying data from the controller; and
    execution of the instructions by the processor further configures the PIOT device to:
        determine a type of the controllable device responsive to the identifying data, from among a plurality of types of controllable devices; and
        adapt the control data signal to the determined type of the controllable device.

4. The PIOT device of claim 1, wherein:
    the data communication receiver is configured to receive identifying data from the controller, and
    execution of the instructions by the processor further configures the processor to:
        access the memory to retrieve data identifying control operations supported by the controller based on the identifying data from the controller; and
        send, via the data communication transmitter, the data identifying control operations to an output device of the user, wherein the control instruction corresponds to a user selection of a control operation from among the identified control operations supported by the controller.

5. The PIOT device of claim 1, wherein:
    the data communication receiver is configured to receive identifying data from the controller, wherein the identifying data comprises data identifying control operations supported by the controller; and
    execution of the instructions by the processor further configures the processor to:
        access the memory to retrieve user preference data for the user associated with the controller, wherein the user preference data comprising a preferred user selection of one or more control operations among the identified control operations supported by the controller; and
        send, via the data communication transmitter, the user preference data to an output of the user device, wherein the control data signal is based at least in part on a user selection corresponding to the one control instruction.

* * * * *